US012564348B2

(12) United States Patent
Dawoud et al.

(10) Patent No.: US 12,564,348 B2
(45) Date of Patent: Mar. 3, 2026

(54) DEVICE AND METHOD FOR DETECTING VENTRICULAR ARRHYTHMIAS BASED ON DUTY CYCLE CHARACTERISTICS

(71) Applicant: Pacesetter, Inc., Sylmar, CA (US)

(72) Inventors: Fady Dawoud, Studio City, CA (US); Yun Qiao, Sunnyvale, CA (US); Wenwen Li, San Jose, CA (US); Kevin J. Davis, Thousand Oaks, CA (US); Chaoyi Kang, Sylmar, CA (US)

(73) Assignee: Pacesetter, Inc., Sylmar, CA (US)

( * ) Notice: Subject to any disclaimer, the term of this patent is extended or adjusted under 35 U.S.C. 154(b) by 752 days.

(21) Appl. No.: 17/717,103

(22) Filed: Apr. 10, 2022

(65) Prior Publication Data

US 2022/0354410 A1      Nov. 10, 2022

Related U.S. Application Data

(60) Provisional application No. 63/184,236, filed on May 5, 2021.

(51) Int. Cl.
| | |
|---|---|
| *A61B 5/352* | (2021.01) |
| *A61B 5/283* | (2021.01) |
| *A61B 5/308* | (2021.01) |

(52) U.S. Cl.
CPC .............. *A61B 5/352* (2021.01); *A61B 5/283* (2021.01); *A61B 5/308* (2021.01)

(58) Field of Classification Search
CPC ................................. A61B 5/361; A61B 5/363
See application file for complete search history.

(56) References Cited

U.S. PATENT DOCUMENTS

| | | | |
|---|---|---|---|
| 8,391,980 | B2 | 3/2013 | Bornzin et al. |
| 8,514,086 | B2 | 8/2013 | Harper et al. |
| 9,216,285 | B1 | 12/2015 | Boling et al. |
| 9,232,485 | B2 | 1/2016 | Wu et al. |
| 9,320,448 | B2 * | 4/2016 | Xi ........................... A61B 5/361 |
| 10,722,704 | B2 | 7/2020 | Min et al. |
| 10,729,346 | B2 | 8/2020 | Qu et al. |
| 10,765,860 | B2 | 9/2020 | Min et al. |
| 10,777,880 | B2 | 9/2020 | Teo et al. |
| 10,874,322 | B2 | 12/2020 | Gill et al. |
| 11,020,036 | B2 | 6/2021 | Dawoud et al. |
| 11,045,643 | B2 | 6/2021 | Fischer et al. |
| 2010/0312131 | A1 * | 12/2010 | Naware ................. A61B 5/287 |
| | | | 600/518 |
| 2011/0004111 | A1 | 1/2011 | Gill et al. |
| 2011/0125206 | A1 | 5/2011 | Bornzin et al. |
| 2012/0046528 | A1 | 2/2012 | Figler et al. |

(Continued)

*Primary Examiner* — George R Evanisko

(74) *Attorney, Agent, or Firm* — Dean D. Small; Carroll, Hoette & Butscher, LLC

(57) ABSTRACT

A computer implemented method and system for detecting an arrhythmia are provided. The method is under control of one or more processors configured with executable instructions. The method obtains far field cardiac activity (CA) signals sensed at electrodes located remote from a heart over a period of time and applies a feature attenuation filter to the CA signals to form modified CA signals. The feature attenuation filter reduces potential T-waves as a feature not of interest. The method calculates a duty cycle (DC) characteristic of the modified CA signals with respect to duty cycle boundaries and detects an arrhythmia based on the DC characteristic.

22 Claims, 9 Drawing Sheets

(56)                    References Cited

U.S. PATENT DOCUMENTS

| 2012/0065527 A1 | 3/2012 | Gill et al. | |
| 2012/0089032 A1 | 4/2012 | Park et al. | |
| 2012/0197149 A1 | 8/2012 | Gill et al. | |
| 2013/0204147 A1 | 8/2013 | Blomqvist et al. | |
| 2013/0218036 A1 | 8/2013 | Ostrow et al. | |
| 2014/0058278 A1 | 2/2014 | Farai et al. | |
| 2014/0275827 A1 | 9/2014 | Gill et al. | |
| 2019/0336026 A1* | 11/2019 | Dawoud | A61B 5/7225 |
| 2021/0020294 A1 | 1/2021 | Bharmi et al. | |

* cited by examiner

DEVICE AND METHOD FOR DETECTING VENTRICULAR ARRHYTHMIAS BASED ON DUTY CYCLE CHARACTERISTICS

RELATED APPLICATION

The present application claims priority to U.S. Provisional Application No. 63/184,236, Titled "DEVICE AND METHOD FOR DETECTING VENTRICULAR ARRHYTHMIAS BASED ON DUTY CYCLE CHARAC-TERISTICS" which was filed on 5 May 2021, the complete subject matter of which is expressly incorporated herein by reference in their entirety.

BACKGROUND

Embodiments of the present disclosure relate generally to implantable medical devices and methods, and more particularly to medical devices configured to detect ventricular arrhythmias.

Today, a large variety of implantable medical devices (IMD) are provided for various cardiac applications. IMDs may be implanted in a subcutaneous pocket, entirely within a chamber of the heart, and elsewhere. The IMD may be coupled to one or more leads having various combinations of electrodes for sensing and delivering therapy. Alternatively, the IMD may be "leadless", and instead include one or more electrodes provided on the housing of the IMD.

IMDs include various types of sensing circuitry that, in combination with a corresponding collection of electrodes, define one or more sensing channels configured to "listen for" different types of signals and different features. Some sensing circuitry/channels are configured to listen to "near field" signals concerning cardiac activity occurring in a local region immediately surrounding the electrodes, such as in a chamber of the heart in which at least one of the sensing electrodes is implanted. Other sensing circuitry/channels are configured to listen to "far field" signals concerning cardiac activity occurring in a remote region spaced a distance away from the sensing electrodes. An example of a far field sensing application includes a subcutaneous implantable cardioverter defibrillator (ICD) that is coupled to one or more leads that are implanted subcutaneously (e.g., above or below the rib cage, but not transvenous). The subcutaneous ICD listens to far field signals corresponding to activity in one or both atrium and/or one or both ventricles. Another example of a far field sensing application represents an implantable cardiac monitor (ICM), located in a pectoral pocket, and includes the sensing electrodes on the housing of the ICM and listens to far field signals corresponding to activity in one or both atrium and/or one or both ventricles. Another example of a far field signal corresponds to a IMD coupled to a transvenous lead with one or more sensing electrodes in one chamber of the heart but is configured to listen to signals from the other chamber of the heart.

The signals collected by the foregoing types of IMDs may also be referred to as electrocardiogram (EGM) signals. The EGM signals collected by sensing electrodes located subcutaneously, not transvenously, are referred to as subcutaneous EGM signals. Sub-cutaneous EGM signals during certain types of fast arrhythmias, such as ventricular fibrillation (VF), are disorganized electrical activation of the heart ventricles and manifest on the subcutaneous EGM signals as very rapid semi-periodic signals with a heart rate typically greater than 200 beats per minute. The subcutaneous EGM signals during VF also exhibit a peak magnitude that is similar or smaller than the peak magnitude exhibited by an R wave during a regular sinus rhythm. A decrease in signal amplitude occurs with continued VF, which can lead to signal undersensing by arrhythmia detection circuitry within the IMD. For example, the arrhythmia detection circuitry may have a programmed sensing threshold that is set to discriminate between a QRS-wave peak during normal sinus rhythm, and a T wave. However, during VF and other related rapid ventricular arrhythmias, the peak amplitudes of the EGM signal may decrease over the course of the VF episode and fall below the programmed sensing threshold, thereby resulting in inadequate sensitivity to detect a VF episode, thereby potentially leading to delayed or aborted defibrillation shock therapy.

A need remains for improved devices and methods that are able to accurately detect fast ventricular arrhythmias based on far field signals.

SUMMARY

In accordance with embodiments herein, a computer implemented method for detecting an arrhythmia is provided. The method is under control of one or more processors configured with executable instructions. The method obtains far field cardiac activity (CA) signals sensed at electrodes located remote from a heart over a period of time and applies a feature attenuation filter to the CA signals to form modified CA signals. The feature attenuation filter reduces potential T-waves as a feature not of interest. The method calculates a duty cycle (DC) characteristic of the modified CA signals with respect to duty cycle boundaries and detects an arrhythmia based on the DC characteristic.

Optionally, the calculating may include determining the duty cycle based on a relation between a measurement window and a segment of the modified CA signals that exceed the duty cycle boundaries. The segment may be defined by an interval of time that represents a sum of a series of intervals during which the modified CA signals exceed the duty cycle boundaries, but do not exceed upper and lower sensitivity thresholds. The segment may be defined by area under the curve of the modified CA signals that falls between the duty cycle boundaries and the upper and lower sensitivity thresholds.

Optionally, the method may utilize the upper and lower sensitivity thresholds in connection with sensing R waves in the CA signals. The DC characteristic may correspond to an amplitude boundary limited duty cycle of the modified CA signals. The method may determine whether the modified CA signals is indicative of an arrhythmia based on the DC characteristic. The obtaining and applying operations may be implemented by an implantable medical device, while the calculating and detecting operations are determined by an external device.

Optionally, the method may apply a primary arrhythmia detection algorithm. The one or more processors may be further configured to utilize the DC characteristic as a confirmation process to deny or verify arrhythmias declared by the primary arrhythmia detection algorithm. The method may dynamically adjust the DC boundaries based on one or more characteristics of interest from the CA signals.

Optionally, the duty cycle boundaries can include a plurality of threshold levels, and the calculating of the method may include determining the duty cycle characteristic based on i) determining a relation between a measurement window and a segment of the modified CA signals that exceed a first threshold level of the plurality of threshold levels, but do not exceed a second threshold level of the plurality of threshold levels, and ii) applying a weight to the modified CA signals within the segment. Optionally, the duty cycle characteristic can be further based on i) determining a relation between the measurement window and a second segment of the modified CA signals that exceed the second threshold level but do not exceed a third threshold level of the plurality of threshold levels, and ii) applying a second weight to the modified CA signals within the second segment, wherein the first and second weights are different with respect to each other.

In accordance with embodiments herein, a system for detecting arrhythmias is provided. The system includes electrodes configured to sense far field cardiac activity (CA) signals over a period of time. The electrodes are configured to be located remote from a heart. The system includes a feature attenuation filtering circuit configured to apply a feature attenuation filter to the CA signals to form modified CA signals. The feature attenuation filter reduces potential T-waves as a feature not of interest. The system includes memory to store specific executable instructions. One or more processors are provided, that when executing the specific executable instructions, are configured to calculate a duty cycle (DC) characteristic of the modified CA signals with respect to duty cycle boundaries and detect an arrhythmia based on the DC characteristic.

Optionally, the one or more processors may be further configured to determine the duty cycle based on a relation between a measurement window and a segment of the modified CA signals that exceed the duty cycle boundaries. The segment may be defined by an interval of time that represents a sum of a series of intervals during which the modified CA signals exceed the duty cycle boundaries, but do not exceed upper and lower sensitivity thresholds. The segment may be defined by area under the curve of the modified CA signals that falls between the duty cycle boundaries and the upper and lower sensitivity thresholds.

Optionally, the sensing circuitry may be configured to utilize the upper and lower sensitivity thresholds in connection with sensing R waves in the CA signals. The DC characteristic may correspond to an amplitude boundary limited duty cycle of the modified CA signals. The one or more processors may be further configured to determine whether the modified CA signals is indicative of an arrhythmia based on the DC characteristic.

Optionally, the electrodes and feature attenuation filtering circuit may be housed within an implantable medical device, while the one or more processors configured to implement the calculating and detecting operations may be housed within an external device. The one or more processors may be further configured to dynamically adjust the DC boundaries based on one or more characteristics of interest from the CA signals. The feature attenuation filtering circuit may represent a bandpass filter having a passband at 8-15 Hz.

Optionally, the one or more processors are further configured to confirm at least one undersensing condition associated with at least one of a primary channel or a secondary channel in advance of determining the duty cycle characteristic, and wherein the at least one undersensing condition includes at least one of sensing R-R intervals on an associated channel or sensing R-wave peak amplitudes on the associated channel. Optionally, the one or more processors are further configured to compare the R-R intervals to a predetermined time duration or to determine that X out of Y of the last R-R intervals are long sensed R-R intervals.

DETAILED DESCRIPTION

Figure 1:
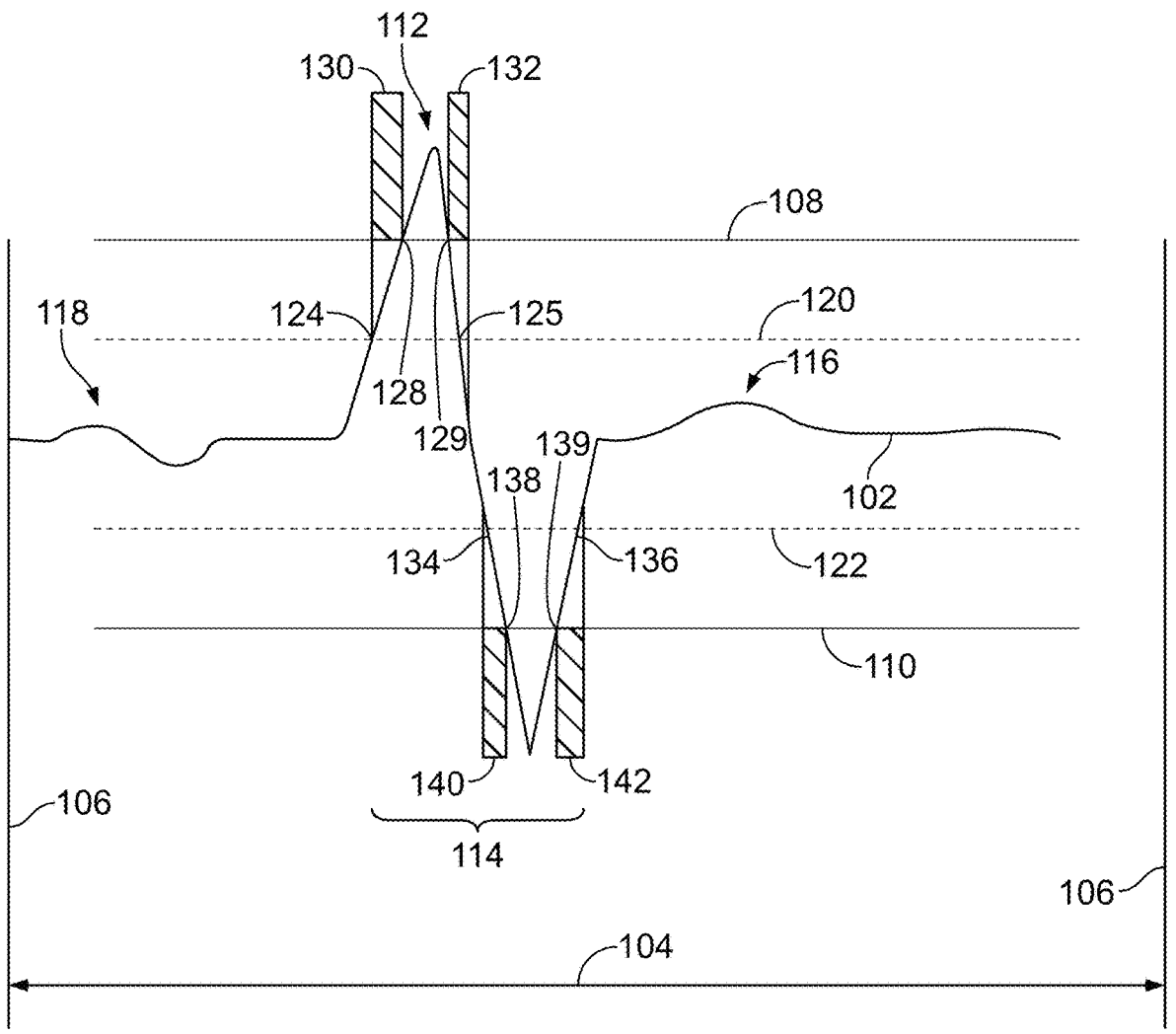
FIG. 1 illustrates an example a cardiac activity signal during a sinus rhythm that exhibits a low duty cycle, as measured in accordance with embodiments herein.

It will be readily understood that the components of the embodiments as generally described and illustrated in the Figures herein, may be arranged and designed in a wide variety of different configurations in addition to the described example embodiments. Thus, the following more detailed description of the example embodiments, as represented in the Figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, appearances of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, etc. In other instances, well-known structures, materials, or operations are not shown or described in detail to avoid obfuscation. The following description is intended only by way of example, and simply illustrates certain example embodiments.

The methods and systems described herein may employ structures or aspects of various embodiments (e.g., systems and/or methods) discussed herein. In various embodiments, certain operations may be omitted or added, certain operations may be combined, certain operations may be performed simultaneously, certain operations may be performed concurrently, certain operations may be split into multiple operations, certain operations may be performed in a different order, or certain operations or series of operations may be re-performed in an iterative fashion. It should be noted that, other methods and systems may be used, in accordance with an embodiment herein. Further, wherein indicated, the methods and systems may be fully or partially implemented by one or more processors of one or more devices or systems. While the operations of some methods and systems may be described as performed by the processor(s) of one device, additionally, some or all of such operations may be performed by the processor(s) of another device described herein.

Terms

The terms "cardiac activity signal", "cardiac activity signals", "CA signal" and "CA signals" (collectively "CA signals") are used interchangeably throughout to refer to an analog or digital electrical signal recorded by two or more electrodes positioned transvenous, subcutaneous or cutaneous, where the electrical signals are indicative of cardiac electrical activity. The cardiac activity may be normal/healthy or abnormal/arrhythmic. Non-limiting examples of CA signals include ECG signals collected by cutaneous electrodes, and EGM signals collected by subcutaneous or transvenous electrodes.

The term "COI" refers to a characteristic of interest within CA signals. Non-limiting examples of COI from a PQRST complex, include an R-wave, P-wave, T-wave and isoelectric segments. Non-limiting examples of COI from CA signals collected at an individual electrode(s) include a sensed event (e.g., an intrinsic event or evoked response). The COI may correspond to a peak of an individual sensed event, R-wave, an average or median P, R or T-wave peak and the like.

The terms "duty cycle" and "DC" shall mean a relation between i) a measurement window and ii) a segment of the modified CA signals that exceeds the duty cycle boundaries. For example, the segment may be defined by an interval of time, from the measurement window, during which the CA signal exceeds duty cycle boundaries. For example, the duty cycle may represent a percentage (%) of time where CA signal is between specific voltage threshold levels over a measurement window (e.g., a number of milliseconds, seconds, heartbeats, peak to peak CA signal changes). As another example, the segment may be defined by area under the curve of the modified CA signals that falls between the duty cycle boundaries and the upper and lower sensitivity thresholds.

The terms "amplitude boundary limited" and "ABL", when used in connection with describing duty cycle, shall mean the intervals of time during which the CA signals have an amplitude that falls within positive or negative amplitude ranges defined by upper and lower duty cycle boundaries and upper and lower sensitivity thresholds. More specifically, the ABL duty cycle of the CA signals corresponds to a sum of the time intervals during which the amplitude of the CA signals exceeds the upper and lower duty cycle boundaries, but does not exceed the upper and lower sensitivity thresholds.

The term "fast", when used in connection with describing an arrhythmia, refers to arrhythmias characterized by a heart rate greater than a normal sinus heart rate (e.g., above 120 bpm, above 200 bpm, etc.).

The terms "sensitivity threshold" and "sensitivity level", are used interchangeably herein, to refer to a threshold that an input CA signal must exceed for an implantable device to identify a CA signal feature of interest (e.g., an R-wave). As one non-limiting example, software may be implemented using a programmed sensitivity level to declare an R-wave to be detected when the input CA signal exceeds the current programmed sensitivity level. In response, the software declares a device documented feature (e.g., R-wave) marker. The sensitivity level may be defined in various manners based on the nature of the CA signals. For example, when the CA signals measure electrical activity in terms of millivolts, the sensitivity level represents a millivolt threshold. For example, when a cardiac beat with a 0.14 mV amplitude is sensed by a device hardware, an R-wave may be detected when the current sensitivity level is programmed to 0.1 mV. However, when the sensitivity level is programmed to 0.15 mV or above, a cardiac beat with amplitude of 0.14 mV will not be detected as an R-wave. The sensitivity threshold/level may be programmed by a clinician or automatically adjusted (e.g., in accordance with the methods and systems described in the below referenced applications Ser. Nos. 15/973,571, 15/973,307, 16/930,791 and 16/399,813). The sensitivity threshold/level may be decreased until reaching a maximum sensitivity.

The term "subcutaneous" shall mean below the skin, but not intravenous. For example, a subcutaneous electrode/lead does not include an electrode/lead located in a chamber of the heart, in a vein on the heart, or in the lateral or posterior branches of the coronary sinus.

The abbreviations "RA", "LA", "RV" and "LV" refer to the right atrium, left atrium, right ventricle and the left ventricle respectively.

Overview

As explained herein, it has been found that in at least some fast arrhythmias, such as certain ventricular arrhythmias, like VF, signal amplitude decreases below conventional sensing thresholds which leads to inappropriate undersensing and withholding of therapy.

In accordance with new and unique aspects herein, methods and devices are described that detect/confirm a presence of treatable fast arrhythmias (VF, monomorphic VT, polymorphic VT) based on CA signals (e.g., EGM signals) collected over one or more subcutaneous sensing channels. The methods and devices utilize a duty cycle characteristic of interest, alone or in combination with, customized filtering of the measured EGM signals, in order to mitigate undersensing CA signal COIs indicative of the arrhythmia of interest. For example, the sensing circuitry may include hardware/firmware that can be reprogrammed for custom hardware-level frequency filtering.

Subcutaneous CA signals (and far-field sensed CA signals in general) measured at a distance from cardiac tissue reflect global cardiac activation patterns and contain components of atrial and ventricular electrical depolarization (activation) and repolarization (relaxation). Ventricular fibrillation (VF) and polymorphic ventricular tachycardia (PVT) are disorganized electrical activation of the heart ventricles and manifest on the CA signals as very rapid semi-periodic signals with a heart rate typically greater than 200 beats per minute and with a peak magnitude similar or smaller than an R-wave peak magnitude during a regular sinus rhythm.

In accordance with new and unique aspects herein, devices and methods account for the decrease in signal magnitude that occurs with onset of VF/PVT. Embodiments herein avoid signal undersensing as would otherwise occur in a conventional arrhythmia detection system that utilized a programmed sensing threshold set to sense a QRS-wave peak, but not a T-wave peak, during a sinus rhythm (SR) or during a supraventricular tachycardia (SVT). Embodiments herein avoid undersensing PVT/VF signals and thereby avoid the potential to unduly delay or incorrectly abort defibrillation shock therapy.

In accordance with new and unique aspects herein, devices and methods are described that take advantage of three properties of PVT/VF signals relative to SR signals, recognized by the applicants, in order to compute a duty cycle-based metric (VF duty cycle, or VFDC) specific to identifying scenarios of VF/PVT undersensing. The properties include i) higher frequency range of PVT/VF signals of interest compared to T-wave not of interest, ii) higher duty cycle of PVT/VF signals and iii) smaller signal amplitude of PVT/VF signals. A VF signal is typically a more sinusoidal (disorganized) voltage signal as opposed to SR/SVT which have segments of high amplitude in R-wave or T-wave portions followed by segments of low amplitudes in P-wave and iso-electric portions. As a result, duty cycle boundaries (e.g., voltage threshold) can be defined such that VF/PVT signals have a relatively higher duty-cycle relative to such duty cycle boundaries, as compared to SR/SVT.

Duty Cycle Based Arrhythmia Detection/Confirmation

FIG. 1 illustrates an example cardiac activity signal during a sinus rhythm that exhibits a low duty cycle, as measured in accordance with embodiments herein. A cardiac signal 102 is illustrated over a period of time corresponding to a measurement window 104, leading and trailing temporal boundaries of which are denoted by the opposed vertical dashed lines 106. Upper and lower sensitivity thresholds 108, 110 represent levels utilized by the sensing circuitry to identify an R-wave 112 (and/or QRS complex 114) within the CA signals 102. For example, the sensing circuit declares detection of an R-wave when the CA signals 102 exceed either of the sensitivity thresholds 108, 110. The QRS complex 114 is followed by a T-wave generally denoted at 116. The QRS complex 114 is preceded by a P-wave generally denoted at 118. The sensitivity thresholds 108, 110 are set to be sensitive only to the R-wave 112, and not the P-wave 118 or T-wave 116.

In accordance with embodiments herein, the CA signal 102 may represent a modified CA signal that is formed when the original incoming raw CA signals are processed by a feature attenuation filter. As explained herein, the feature attenuation filter may represent a bandpass filter having a passband set to generally correspond to a frequency range normally associated with ventricular arrhythmias of interest such as VF. As one nonlimiting example, the bandpass filter may have a passband between 10 and 20 Hz, and more preferably between 8 and 15 Hz. The lower limit of the passband is set to generally attenuate frequency components below the lower limit, which are common within the T wave of a sinus rhythm. PVT/VF signals generally include frequency content within a frequency range that is slightly higher than the frequency range associated with the T wave of a sinus rhythm. For example, PVT/VF signals may have frequency content within the range of 1-15 Hz, with the majority of the frequency content above 8 Hz. Sinus rhythm T waves have frequency content with the range of 1-10 Hz, with a majority of the frequency content below 8 Hz. Returning to the example of FIG. 1, the feature attenuation filter did not have a substantial impact on the amplitude of the QRS complex 114, but did significantly attenuate the T wave 116.

Alternatively, embodiments herein may implement the duty cycle calculation upon the original incoming raw CA signal, without performing the foregoing bandpass filtering and attenuation.

In accordance with embodiments herein, devices and methods calculate a duty cycle (DC) characteristic of the modified CA signals with respect duty cycle boundaries. FIG. 1 illustrates additional boundaries that are defined to be separate and distinct from the sensitivity thresholds 108, 110. The additional boundaries are referred to as duty cycle boundaries and are denoted as dashed lines at 120, 122. The duty cycle boundaries 120, 122 represent upper and lower (positive and negative) voltage levels that are utilized to calculate the DC characteristic for the CA signal 102. The DC boundaries 120 and 122 are set at levels below/within the sensitivity thresholds 108, 110.

FIG. 1 further illustrates a graphical representation of the calculation performed herein to determine the duty cycle characteristic of the modified CA signals 102 with respect to the duty cycle boundaries 120, 122. The time duration of interest for the duty cycle characteristic, represents the amount of time that the CA signals has an amplitude between the DC boundaries 120, 122 and sensitivity thresholds 108, 110, namely while the CA signals exceed the duty cycle boundaries 120, 122, but still falls below the sensitivity thresholds 108, 110. With reference to FIG. 1, during the QRS complex, the CA signals cross and exceed the upper DC boundary 120 at the point denoted 124 and continue to rise until crossing and exceeding the upper sensitivity threshold 108 at 128. The CA signal remains above the upper sensitivity threshold 108 until dropping below the upper sensitivity threshold 108 at 129. The CA signal continues to decrease until falling below the upper DC boundary 120 at 125. The CA signal then continues until becoming negative and crossing the lower DC boundary 122 at 134. The CA signal remains between the lower DC boundary 122 and a lower sensitivity threshold 110 until crossing the lower sensitivity threshold 110 at 138. The CA signal remains below the lower sensitivity threshold 110 until beginning to rise and crossing the lower sensitivity threshold 110 at 139. The CA signal remains between the lower DC boundary 122 and lower sensitivity threshold 110 until crossing above the lower DC boundary 122 at 136. The intervals of time 130 and 132 represent the short intervals of time during which the CA signal has an amplitude between the upper DC boundary 120 and upper sensitivity threshold 108. The intervals of time 140 and 142 represent the short intervals of time during which the CA signal has an amplitude between the lower DC boundary 122 and lower sensitivity threshold 110. The series of intervals 130, 132, 140 and 142 are summed to obtain a total interval of time, from the measurement window 104, during which the modified CA signals have an amplitude between the DC boundaries and the corresponding sensitivity thresholds. The duty cycle characteristic is then calculated as percentage (%) of time where CA signals exceed the DC boundaries, but do not exceed the sensitivity thresholds over a measurement window.

The duty cycle characteristic is calculated based on duty cycle boundaries by determining a relation between i) an overall duration of a measurement window 104 and ii) an interval of time (e.g., a sum of a series of intervals), from the measurement window 104, during which the modified CA signal exceeds duty cycle boundaries but does not exceed upper and lower sensitivity thresholds. The measurement window 104 extends between the lines 106 and for example may correspond to one or more milliseconds, one or more seconds, one or more heartbeats, a number of peak to peak changes in the CA signal and the like.

Figure 2:
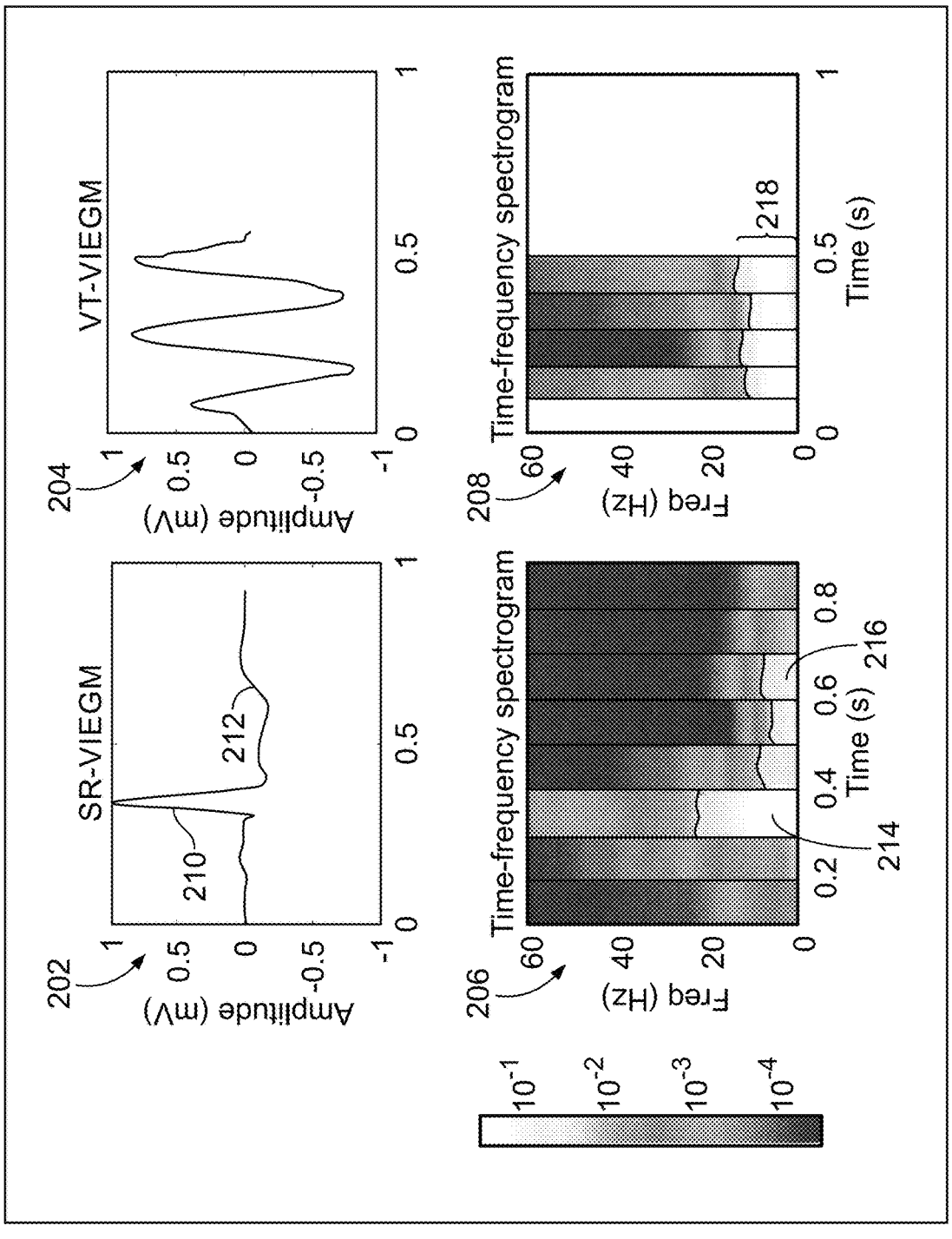
FIG. 2 illustrates a comparison of certain characteristics between a sinus rhythm and a ventricular arrhythmia utilized in accordance with embodiments herein.

FIG. 2 illustrates a comparison of certain characteristics between a sinus rhythm and a ventricular arrhythmia utilized in accordance with embodiments herein. The upper left panel 202 illustrates CA signals, over a measurement window, for a sinus rhythm having an R-wave 210 and a T-wave 212. The upper right panel 204 illustrates CA signals, over a measurement window, for one of a polymorphic ventricular tachycardia or ventricular fibrillation. The lower left panel 206 illustrates a Fourier transform of the sinus rhythm CA signals, while the lower right panel 208 illustrates a Fourier transform of the PVT/VF CA signals. The Fourier transforms 206, 208 of the lower panels illustrate time along the horizontal axis corresponding to the horizontal time axis of the CA signals in the upper panels 202, 204. The vertical axis of the lower panels 206, 208 correspond to frequency components. The Fourier transforms 206, 208 are divided into vertical time bars corresponding to short periods of time over the measurement window of the upper panels 202, 204. Each gray scale vertical bar plots a power or energy content associated with the frequency components during the corresponding segment of time from the sinus rhythm or PVT/VF CA signals.

For example, in the lower left panel 206, during the R-wave 210, the corresponding segment of time from the time Fourier transform to CA signals exhibits the largest relative amount of energy (as denoted at 214) in the frequency range up to approximately 20 Hz. The T wave 212 exhibits the largest relative amount of energy (as denoted at 216) in the frequency range of 1-10 Hz.

In the lower right panel 208, the time Fourier transform of the PVT/VF episode is also divided into segments over the measurement window. Each of the segments over the measurement window exhibit similar, and relatively large, amounts of energy in the frequency range of 1-15 Hz (as denoted at 218).

As shown in the upper panels 202, 204, the PVT/VF signal is typically a more sinusoidal (albeit disorganized) voltage signal as opposed to SR/SVT CA signals which have segments of high amplitude in R-wave or T-wave portions followed by segments of low amplitudes in P-wave and iso-electric portions. As a result, PVT/VF signals have relatively higher duty-cycle (e.g., % of time where the CA signal is between specific voltage threshold levels). FIG. 1 shows an example of low duty cycle during SR. In addition, the PVT/VF signals also tend to have similar or smaller voltage amplitude compared to R waves during sinus rhythm and a slightly higher frequency range compared to sinus rhythm T-wave (e.g., 1-15 Hz for PVT/VF vs 1-10 Hz for T-wave SR). As explained herein, a customized frequency filter in the range of 1-10 Hz is configured to attenuate more of the T-wave compared to PVT/VF.

Figure 3:
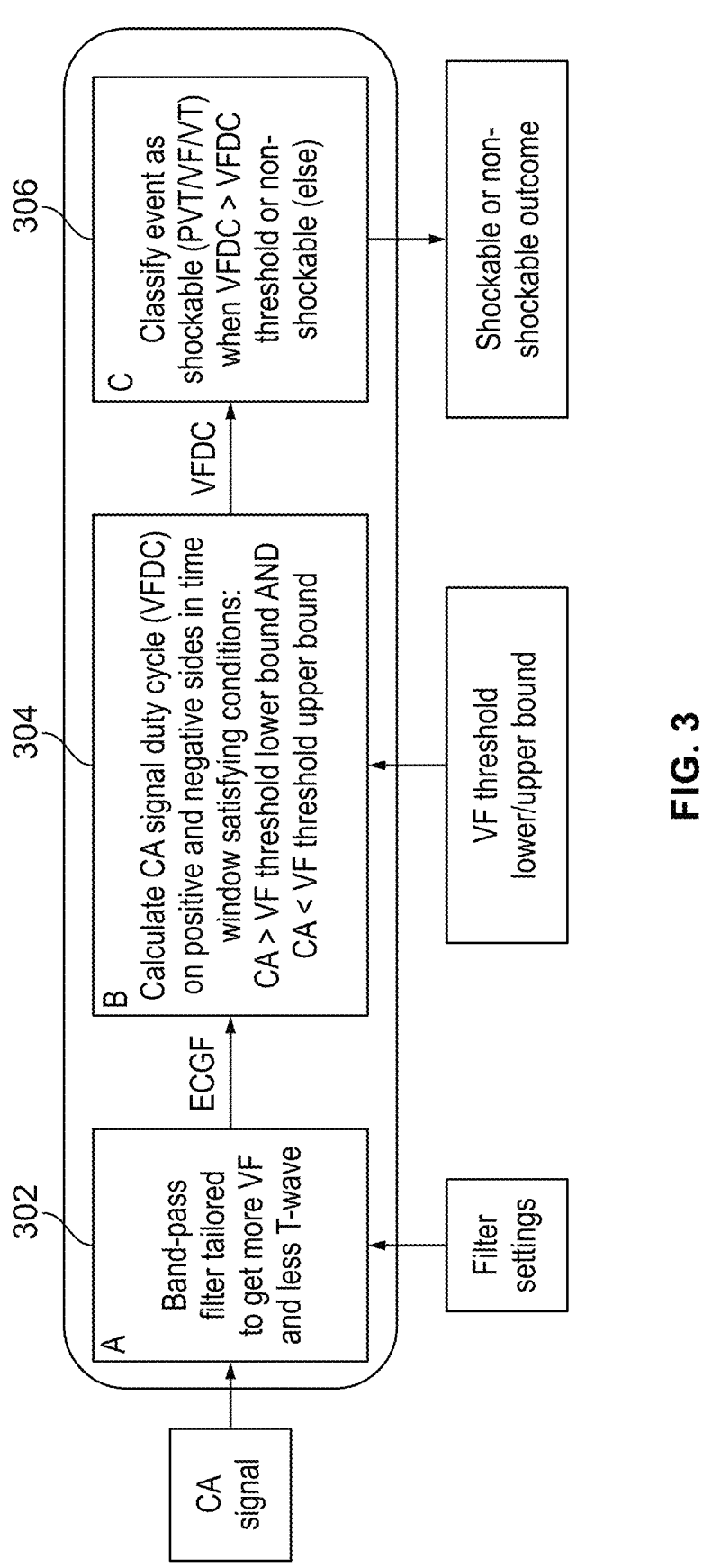
FIG. 3 shows a flow diagram of a method for detecting arrhythmias in accordance with embodiments herein.

FIG. 3 shows a flow diagram of a method for detecting arrhythmias in accordance with embodiments herein. The method may be implemented by a combination of circuitry, firmware and one or more processors executing programmable instructions, and may be wholly or partially implemented by an implantable medical device, a local external device, a remote server or other computing device. The method may be implemented as a primary arrhythmia detection algorithm to identify the presence of shockable arrhythmias while in the presence of undersensing by the main sensing channel/circuitry. Additionally or alternatively, the method may be implemented as a confirmation process, such as one operating in parallel with a separate primary arrhythmia detection algorithm, where the confirmation process seeks to identify/confirm a presence of a shockable arrhythmia (or lack thereof).

At 302, the process applies a feature attenuation filter, such as through a filtering circuit that obtains far field CA signals (e.g., EGM signals) sensed at electrodes located remote from the heart. While the CA signals are received continuously, the discussion in connection with FIG. 3 is described relative to a period of time, such as a measurement window as discussed hereafter. The filtering circuit receives filter settings to configure the filter as a bandpass filter that is tailored to increase or at least minimalize an amount of attenuation applied to an arrhythmia feature of interest, such as a ventricular arrhythmia, PVT, etc. The filter settings further configure the bandpass filter to attenuate features that are not of interest, such as the T-wave. By way of example, the filter settings may define the bandpass filter to retain PVT/VF frequencies (e.g., 8-15 Hz) while reducing contribution of T-wave (e.g., 1-10 Hz).

The filtering circuitry outputs a modified CA signal that has been band pass filtered to attenuate frequency content below a lower cut off frequency (e.g., 8 Hz). Optionally, the modified CA signal may be bandpass filtered to attenuate frequency content above an upper cut off frequency (e.g., equal to or greater than 15 Hz). When the CA signals include a PVT/VF, the modified CA signals still contain frequency components associated with PVT/VF that are not attenuated.

The feature attenuation filter may be customized on a patient-by-patient level given the capabilities of the filtering hardware platform. For example, a firmware update may be applied to change the bandpass filter cutoff frequencies as well as other characteristics of the filter performance. As further examples, an initial firmware setting may be applied to the filter circuitry based on a patient population. Thereafter, the firmware settings may be adjusted for the individual patient at the time of implant, shortly after implant or periodically throughout the life of the implant, such as during patient visits to the clinician.

At 304, one or more processors calculate a DC characteristic of the modified CA signals with respect to duty cycle boundaries. For example, the one or more processors determine the duty cycle based on a relation between an overall duration of a measurement window and an interval of time, from the measurement window, when the modified CA signals exceed the duty cycle boundaries. The interval of time may represent a sum of a series of intervals during which the modified CA signals exceed the duty cycle boundaries, but do not exceed upper and lower sensitivity thresholds.

The DC characteristic represents an amplitude boundary limited (ABL) DC characteristic as the one or more processors calculate the intervals of time during which the CA signals have an amplitude that falls within positive or negative amplitude ranges defined by upper and lower duty cycle boundaries and upper and lower sensitivity thresholds. The one or more processors sum the time intervals during which the amplitude of the CA signals exceeds the upper and lower duty cycle boundaries, but does not exceed the upper and lower sensitivity thresholds. The upper and lower sensitivity thresholds represent the sensitivity threshold utilized by the sensing circuitry for the primary/main sensing channel in connection with sensing R waves in the CA signals. The sensitivity threshold/level may be programmed by a clinician or automatically adjusted (e.g., in accordance with the methods and systems described in the below referenced applications Ser. Nos. 15/973,571, 15/973,307, 16/930,791 and 16/399,813). The sensitivity threshold/level may be decreased until reaching a maximum sensitivity, which is below the DC boundaries. Stated another way, the DC boundaries have positive and negative voltage levels, respectively, that fall between the sensitivity threshold/level and the maximum sensitivity.

The sum is then divided by the duration of the measurement window to obtain the final DC characteristic, which may also be referred to as a ventricular frequency duty cycle (VFDC), such as when the far field CA signals correspond to ventricular activity.

The amplitude levels for the DC boundaries and the sensitivity thresholds (lower bound and upper bound applied for both positive and negative sides of voltage signal) are selected to exclude portions of the filtered/modified CA signals that are either too large (e.g., noise and sinus R-wave segments) or too small (e.g., isoelectric and P-wave segments). Only CA signals samples between the DC boundaries and sensitivity thresholds are included in the duty cycle metric (VFDC) calculation.

Additionally or alternatively, the DC boundaries (e.g., VF upper bound and VF lower bound) can be either constant or programmable (e.g., baseline threshold=0.035 mV). Additionally or alternatively, the DC boundaries may also be defined relative to the programmed sensing threshold. (e.g., VF lower bound threshold=30% of the sensitivity threshold, while VF upper bound threshold=125% of the sensitivity threshold).

At 306, the one or more processors detect an arrhythmia based on the DC characteristic. For example, the one or more processors compare the VFDC (or more generally DC characteristic) to one or more thresholds. When the DC characteristic exceeds the DC threshold, the one or more processors detect an arrhythmia to be present. Optionally, different DC thresholds may be utilized to distinguish between different arrhythmias. By way of example, the DC threshold may be set as a percentage (e.g., VFDC TH, 0% to 100%) and used to classify events as shockable or non-shockable. Thereafter, the one or more processors output a determination that the CA signals are indicative of a shockable arrhythmia or alternatively a non-shockable rhythm, where the non-shockable rhythm may be a sinus rhythm or an abnormal rhythm. For example, shockable rhythms may represent monomorphic VT, polymorphic VT, or ventricular fibrillation. Examples of non-shockable rhythms may represent a sinus rhythm, a supraventricular tachycardia, or even simply noise and the like.

Figure 4A:
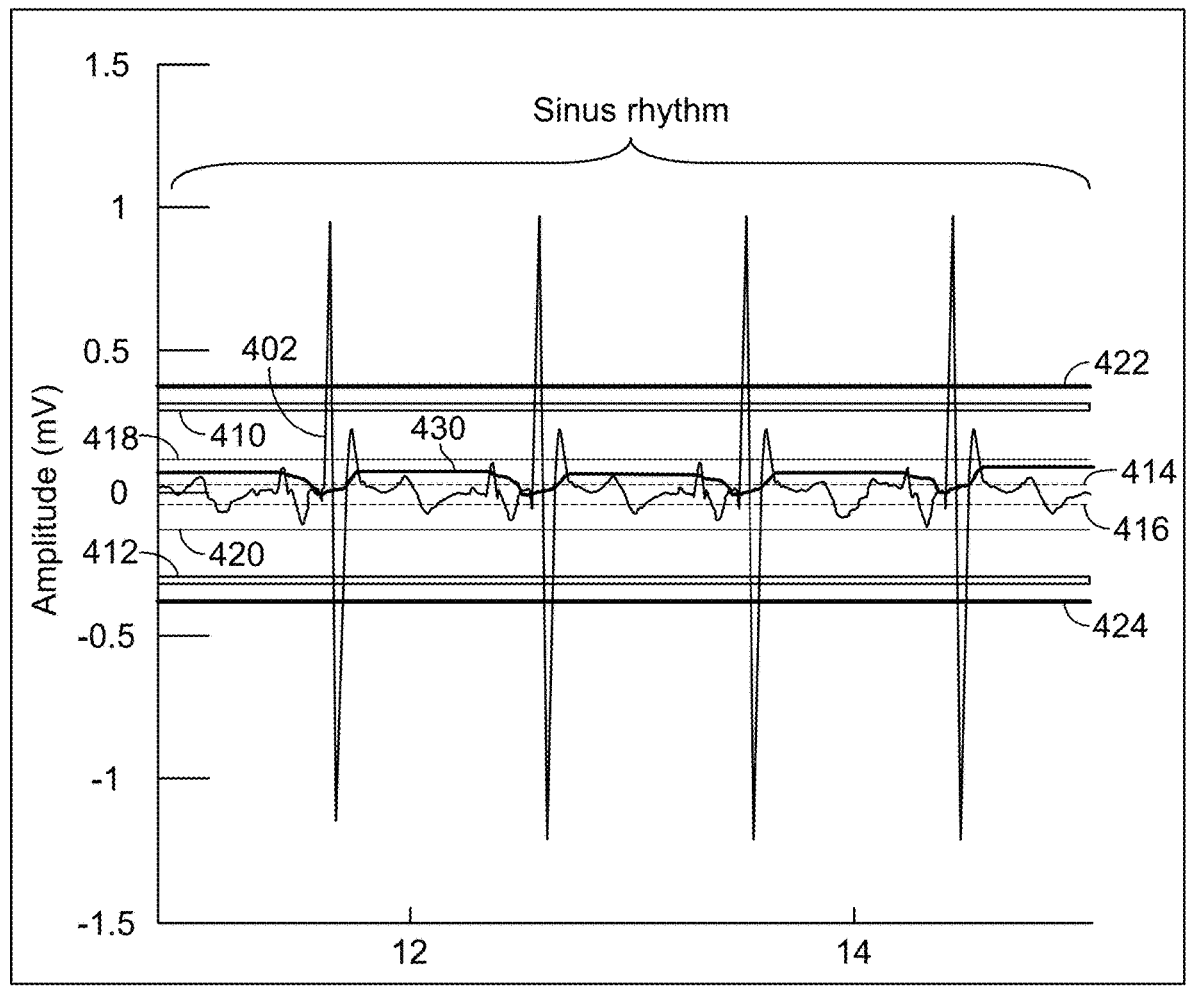
FIG. 4A shows an example applying the methods and devices described herein in connection with CA signals exhibiting a sinus rhythm.
Figures 4B, 4C:
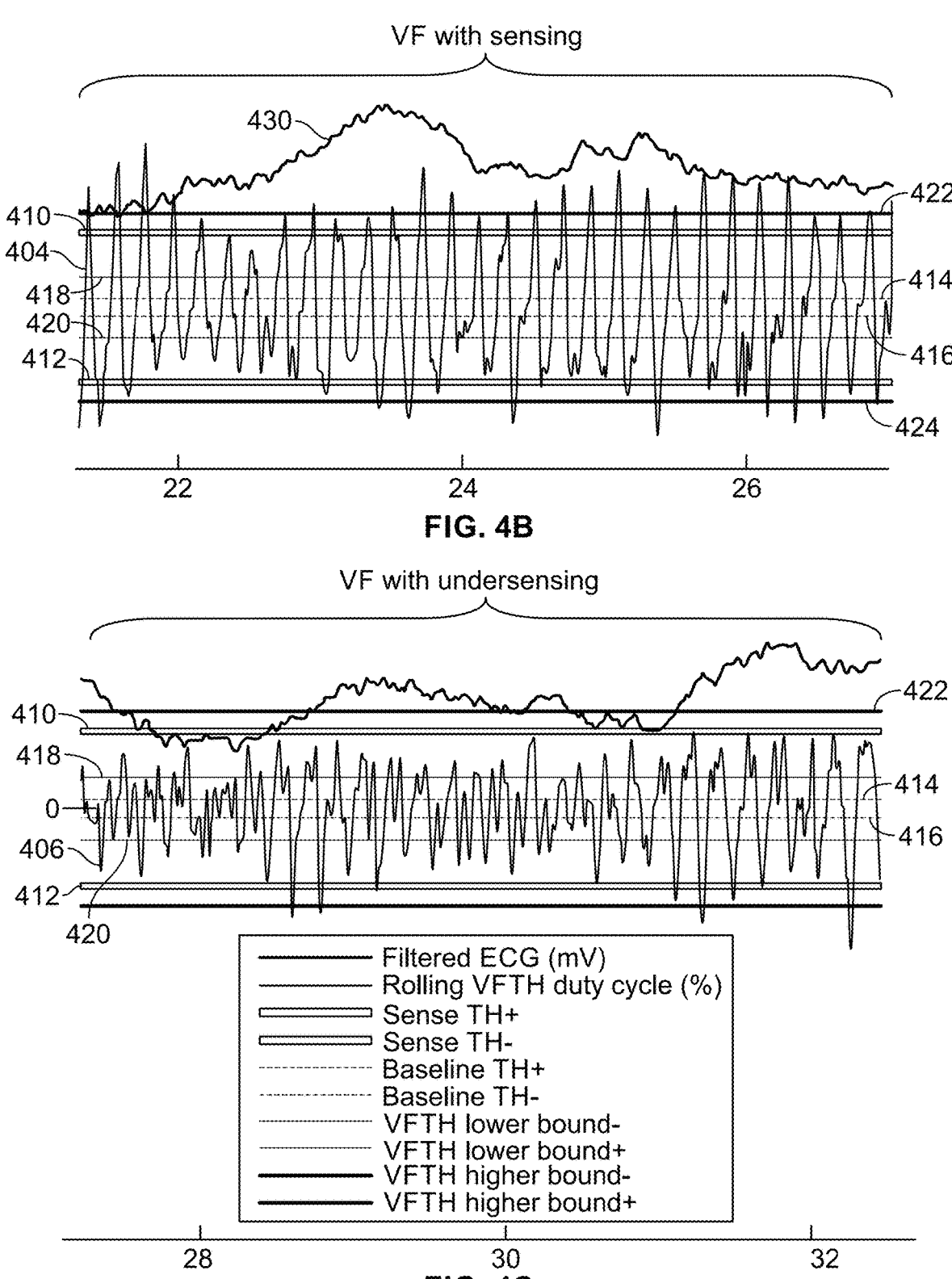
FIG. 4B shows an example applying the methods and devices described herein in connection with VF signal sensing.
FIG. 4C shows an example applying the methods and devices described herein in connection with CA signals exhibiting VF with signal undersensing.

FIG. 4A shows an example applying the methods and devices described herein in connection with CA signals exhibiting a sinus rhythm. FIG. 4B shows an example applying the methods and devices described herein in connection with VF signal sensing. FIG. 4C shows an example applying the methods and devices described herein in connection with CA signals exhibiting VF with signal undersensing. The original CA signals are filtered by a bandpass filter (e.g., 8-15 Hz) to reduce the T-wave frequency content and retain potential VF frequency content. FIGS. 4A-4C illustrate modified CA signals 402, 404 and 406. FIGS. 4A-4C further illustrate upper and lower sensitivity thresholds 410, 412, baseline sensitivity limits (e.g., maximum sensitivity threshold) 414, 416, and DC boundaries 418, 420. Optionally, the DC boundaries 418, 420 may be defined as inner DC boundaries, while adding outer DC boundaries 422, 424. For example, the DC characteristic may be calculated for time intervals during which the modified CA signals 402 remain between the inner DC boundaries 418, 420 and the outer DC boundaries 422, 424, without reference to the sensitivity threshold 410, 412.

FIGS. 4A-4C further illustrate a rolling duty cycle characteristic 430 which is calculated repeatedly over successive beats. With reference to FIG. 4A, the rolling DC characteristic maintains a relatively small level, such as less than 10%, during normal sinus rhythms. Turning to FIG. 4B, the modified CA signal 404 corresponds to ventricular fibrillation in which the amplitudes of the VF events are sufficient to cross the sensitivity thresholds 410, 412. Each time the CA signals cross the sensitivity thresholds 410, 412, the primary sensing circuit detects the VF event (herein generally referred to as VF with sensing), which would result in a determination of VF based on the rate between successive VF events (e.g., utilizing a conventional VF detection algorithm). The CA signals exhibit substantially more content between the DC boundaries 418, 420 and the sensitivity thresholds 410, 412, and thus have a higher duty cycle characteristic as compared to the sinus rhythm of FIG. 4A. By way of example, the DC characteristic may exhibit a duty cycle of 40-80% during VF with sensing.

Returning to FIG. 4C, the modified CA signal 406 corresponds to a ventricular fibrillation in which the amplitudes of the VF events are lower (as compared to FIGS. 4A and 4B) and do not cross the sensitivity thresholds 410, 412 (herein generally referred to as VF with undersensing). As shown in FIG. 4C, as the VF episode becomes more disorganized, the CA signal amplitude decreases below the programmed sensitivity threshold (0.3 mV). In this example, the primary sensing circuit would not detect the VF event if the sensitivity thresholds 410, 412 were maintained. The CA signals of FIG. 4C still exhibit more content between the DC boundaries 418, 420 and the sensitivity thresholds 410, 412, although not as much content as compared to VF with sensing of FIG. 4B. By way of example, the DC characteristic 430 may exhibit a duty cycle of 20-60% during VF with undersensing. In accordance with the foregoing nonlimiting examples, the threshold utilized at 306 to classify an event may be set to 20% or higher to detect VF with undersensing based on the DC characteristic. As another example, the threshold may be set to 40% or higher to detect VF with sensing based on the DC characteristic.

In other embodiments, methods and devices can utilize multiple threshold bands (e.g., segments) defined between identified threshold levels (e.g., voltage threshold levels, duty cycle boundaries, etc.) to calculate the duty cycle-based metric (e.g., VFDC). Therefore, the plurality of threshold levels defining the multiple threshold bands can also be referred to as the duty cycle boundaries and the amplitude boundary limited characteristics, similar to the ABL DC characteristics discussed previously. Using the threshold bands can, for example, determine whether the modified CA signal 402 is on or off for duty cycle purposes. For example, the metric value increases with borderline sensing, decreases with very good sensing (e.g., R-wave amplitude high or very high compared to, for example, the upper/lower sensitivity thresholds 410, 412), and ignores baseline/P-wave signal level. In the discussion below, the calculations are accomplished at least in part on absolute values of the modified CA signal 402, and thus only one set of multiple threshold levels (e.g., positive voltage threshold levels and/or positive duty cycle boundaries) and the multiple threshold bands defined therebetween are discussed.

In this example, five threshold levels are used. However, in some embodiments more or fewer than five threshold levels can be used, and the threshold levels can be set at different levels relative to, for example, the maximum sensitivity threshold 414 and upper sensitivity threshold 410. In some embodiments, one or more of the five threshold levels can be referred to interchangeably with the duty cycle boundaries, wherein data is calculated between two of the threshold levels (e.g., one of the threshold levels can be referred to as the duty cycle boundary, data is calculated between first and second threshold levels, etc.) or between one of the threshold levels and the maximum sensing threshold 414 (e.g., the maximum sensing threshold 414 can be interchangeable with the duty cycle boundary).

By way of example, the levels of the five threshold levels can be set as follows, but are not so limited. A low VFDC threshold is set above iso-electric segment and P-wave level. The low VFDC threshold can be set below the maximum sensitivity threshold 414 (e.g., approximately 30% of maximum sensitivity threshold 414). A medium VFDC threshold can be set slightly above the upper sensitivity threshold 410 (e.g., approximately 175% of maximum sensitivity threshold 414). A high VFDC threshold can be set further above the upper sensitivity threshold 410 (e.g., approximately 225% of maximum sensitivity threshold 414), and a very high VFDC threshold can be set above the high VFDC threshold (e.g., approximately 450% of maximum sensitivity threshold 414). In this example, the very high VFDC threshold can function as two thresholds, wherein data is analyzed below and above the very high VFDC threshold.

The VFDC metric (e.g., DC characteristic) is calculated on ranges of data (e.g., segments, bands) between the multiple threshold levels within the most recent window of time (e.g., 0.75 seconds) of buffered data. A weighted sum is used to calculate the weighted VFDC metric, such as by using weights of approximately 0, +1, −1, −1.2 and −1.5 for bands or segments, defined with respect to the maximum sensitivity threshold 414, of 0-30%, 30-175%, 175-225%, 225-450% and >450%, respectively. In some embodiments, the weighted sum can be calculated as follows: i) 0*percentage (%) of time while absolute modified CA signals 402 (e.g., absolute narrowband filtered ECG signal) are between 0 and 0.3 times the maximum sensitivity threshold 414 (e.g., exceed a first threshold level but do not exceed a second threshold level); ii) +1*percentage (%) of time while absolute modified CA signals 402 are between 0.3 times the maximum sensitivity threshold 414 and 1.75 times the upper sensitivity threshold 410 (e.g., exceed the second threshold level but do not exceed a third threshold level); iii) −1*percentage (%) of time while absolute modified CA signals 402 are between 1.75-2.25 times the maximum sensitivity threshold 414 (e.g., exceed the third threshold level but do not exceed a fourth threshold level); iv) −1.2*percentage (%) of time while absolute modified CA signals 402 are between 2.25-4.5 times the maximum sensitivity threshold 414 (e.g., exceed the fourth threshold level but do not exceed a fifth threshold level); and v) −1.5*percentage (%) of time while absolute modified CA signals 402 are greater than 4.5 times the maximum sensitivity threshold 414 (e.g., exceed the fifth threshold level). It should be understood that the weights are examples only, and that other values, both positive and negative, are contemplated. As discussed above with respect to FIG. 3, in some embodiments, the threshold to classify an event may be set to 20% or higher to detect VF with undersensing based on the weighted VFDC metric.

Figure 4D:
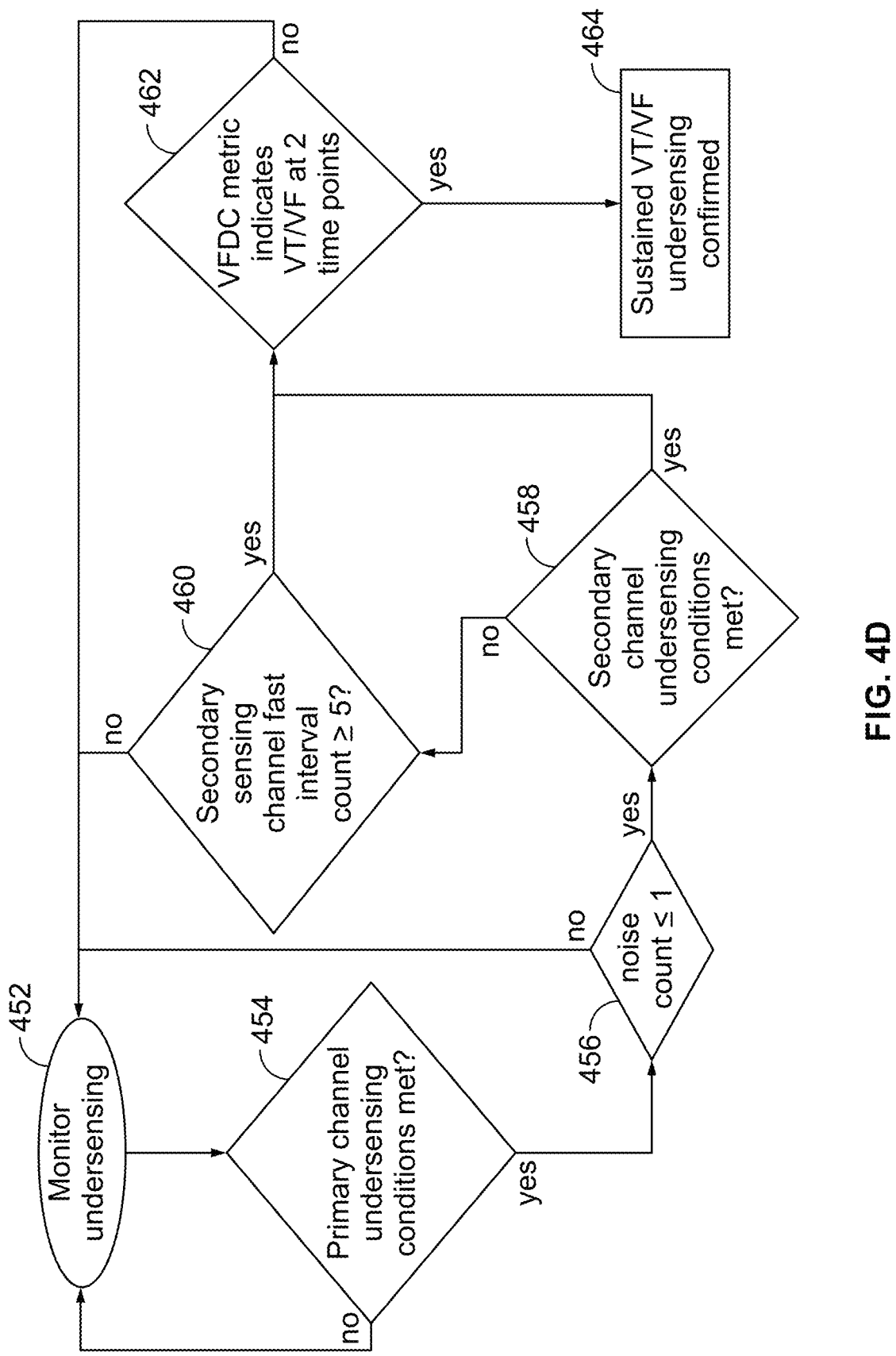
FIG. 4D shows a flow diagram of a method for determining if undersensing of VT/VF is occurring in accordance with embodiments herein.

FIG. 4D shows a flow diagram of a method for determining if undersensing of VT/VF is occurring in accordance with embodiments herein. The method of FIG. 4D can incorporate the VFDC metric into a continuous monitoring implementation. The method may be implemented by a combination of circuitry, firmware and one or more processors executing programmable instructions, and may be wholly or partially implemented by an implantable medical device, a local external device, a remote server or other computing device. The method may be implemented as a primary arrhythmia detection algorithm to identify the presence of shockable arrhythmias while in the presence of undersensing by the main sensing channel/circuitry. Additionally or alternatively, the method may be implemented as a confirmation process, such as one operating in parallel with a separate primary arrhythmia detection algorithm, where the confirmation process seeks to identify/confirm a presence of a shockable arrhythmia (or lack thereof).

At 452, one or more processors can start the method for monitoring for undersensing of VT/VF. At 454, the one or more processors determine whether primary channel undersensing conditions are met, such as discussed previously, and additional information can be calculated to determine if undersensing of VT/VF is occurring. For example, the one or more processors can determine results/outcomes of a first undersensing condition such as by sensing long R-R interval (s) on the primary sensing channel. For example, the first undersensing condition may be satisfied when one long R-R interval is sensed, such as an R-R interval of a predetermined time duration (e.g., greater than two second) and/or X out of the last Y R-R intervals are long sensed R-R intervals (e.g., 2 out of the last 5 R-R intervals, etc.). The one or more processors can also determine results/outcomes of a second undersensing condition, for example, by determining that X out of Y (e.g., 2 out of 5) last sensed R-wave peak amplitudes are within approximately 15% (or other predetermined percentage) of primary sense channel maximum sensitivity. If the primary channel undersensing conditions are not met, flow returns to 452. If the primary channel undersensing conditions are met, additional evaluations can be performed at 456 to confirm VF/VT undersensing in the preceding 5 seconds of buffered data. This time interval is not limiting as other time intervals of buffered data are contemplated.

At 456, the one or more processors can determine if a count of noise beats in the last X beats is <Y (e.g., <=1 noise beat in the last 3 beats). For example, the number of noise beats can be an indication of how "noisy" the signal is, such as from power line interference, physical movement, and the like. If the noise beat count is not <=1, the one or more processors determine that the VF/VT undersensing is not occurring and flow passes to 452. If the noise beat count is <=1, flow passes to 458.

At 458, the one or more processors determine if secondary channel undersensing conditions are met. For example, one secondary channel undersensing condition is determining if the long sensed R-R intervals on the secondary sensing channel exceed parameters (e.g., 1 R-R>2 seconds or 2 out of the last 5 R-R>1.5 seconds, etc.). A second secondary channel undersensing condition is determining if X out of Y (e.g., 2 out of 5) of the last sensed R-wave peak amplitudes are within 15% of secondary sense channel maximum sensitivity. If the undersensing conditions on the secondary sensing channel are not met, flow passes to 460, and if the undersensing conditions are met, flow passes to 462.

At 460, the one or more processors count fast R-R intervals on the secondary sensing channel. If the count of fast R-R intervals (determined relative to a tachycardia rate cut-off) are greater than or equal to a predetermined number, such as 5, flow passes to 462.

At 462, the one or more processors calculate the VFDC metric associated with the multiple bands defined by the multiple thresholds (e.g., thresholds such as low, medium, high, and very high VFDC thresholds described above). If the VFDC metric indicates that an arrhythmia (e.g., VT and/or VF) is occurring, such as at two points in time within a measurement window (e.g., within the previous 5 seconds), the flow passes to 464 and the one or more processors confirm that sustained VT/VF undersensing is occurring and therapy initiation can proceed accordingly. If sustained undersensing is not occurring, flow returns to 452.

In accordance with the foregoing, methods and devices are described that may be utilized as a main/primary arrhythmia detection algorithm that avoids undersensing in certain conditions as experienced by conventional arrhythmia detection algorithms. Additionally or alternatively, the methods and devices here may be utilized as a confirmation process to either confirm an arrhythmia detected by a main/primary detection algorithm or to confirm a lack of an arrhythmia determined by the main/primary detection algorithm.

Figure 5:
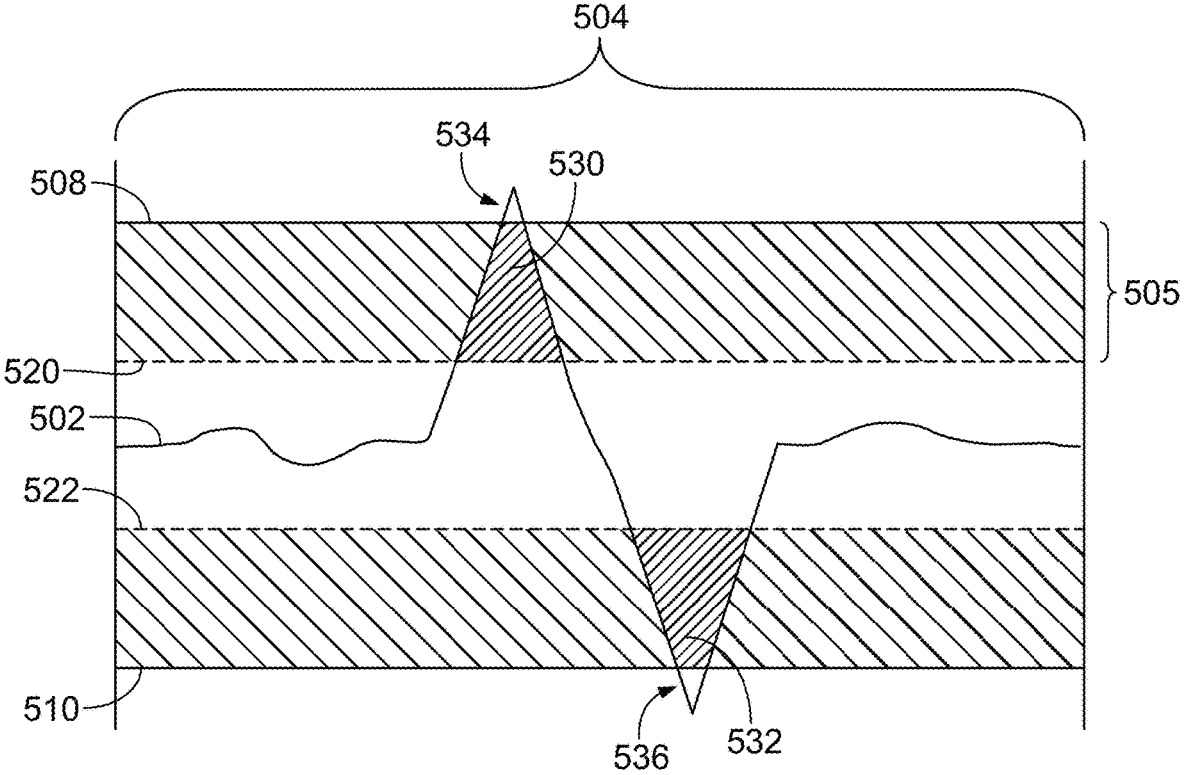
FIG. 5 illustrates a graphical representation of an alternative manner for calculating the duty cycle characteristic based on an area within the CA signals, instead of being based on time intervals, in accordance with embodiments herein.

FIG. 5 illustrates a graphical representation of an alternative manner for calculating the duty cycle characteristic based on an area within the CA signals, instead of being based on time intervals, in accordance with embodiments herein. A modified CA signal 502 is illustrated over a period of time corresponding to a measurement window 504. Upper and lower sensitivity thresholds 508, 510 are utilized by the sensing circuitry to identify an R-wave (and/or QRS complex) within the CA signals 502.

The duty cycle boundaries 520, 522 represent upper and lower (positive and negative) voltage levels that are utilized to calculate the DC characteristic for the CA signal 502. An area of the measurement window is defined as the duration of the measurement window 504 times the amplitude difference 505 between the duty cycle boundary 520 and the sensitivity threshold 508. In accordance with an alternative embodiment, the methods and devices calculate the DC characteristic by determining a relation between an area of the measurement window and a segment of the modified CA signals that exceeds the DC boundaries. The segment is defined by an area of regions 530, 532 (denoted in a narrow crosshatch). The regions 530, 532 represent the area under the curve of the modified CA signals 502 that falls between the duty cycle boundaries 520, 522 and the upper or lower sensitivity thresholds 508, 510. The area of the regions 530, 532 may be summed and divided by the area of the measurement window to obtain an alternative characterization of the DC characteristic. The portion of the waves (denoted at 534, 536) which exceed the sensitivity thresholds 508, 510 represent an area that is excluded from the segment area calculation as the portions 534, 536 have the potential to be part of a sinus rhythm or a T-wave.

Optionally, in accordance with alternative embodiments, the duty-cycle characteristic may be calculated on a rolling window basis, in which the measurement window is incremented successively by short durations (less than the full length of the measurement window). For example, if the measurement window is 100 ms in length, the measurement window may be incremented 10 ms during successive calculations, for each of which the processes described herein are repeated to calculate a new DC characteristic value.

Additionally or alternatively, the DC characteristic may be calculated on-demand for a number of measurement windows to confirm presence of PVT/VF with or without undersensing. For example, the on-demand calculation may be initiated based on a determination, by a primary detection algorithm, that CA signals exhibit a potential PVT/VF. As another example, the on-demand analysis may be initiated by communications from an external device, such as by communication from a bedside monitor, while a patient is sleeping, by the patient via the patient's smart phone or other portable device, by a clinician during in office visit and the like.

Additionally or alternatively, in accordance with embodiments herein, the DC boundaries may be dynamically adjusted based on one or more characteristics of interest from the CA signals. For example, embodiments may determine stability criteria for an article or interval (e.g., R-wave rate) and/or R-wave amplitude. The stability criteria may be calculated on a regular schedule or dynamically in response to various criteria or external commands. Based on the stability criteria, the upper and lower DC boundaries may be adjusted (e.g., increased or decreased). For example, during sinus rhythm and stable ventricular rate/amplitude that is maintained within a 5% tolerance, the methods and devices may update the upper and lower DC boundaries on regular intervals of 4 hours by increasing or decreasing the DC boundaries until the corresponding duty cycle characteristic is <10%. For example, when normal sinus rhythms occur, but the DC characteristic is determined to be 11%, 12% or higher, the DC boundaries may be incrementally increased (e.g., by steps of 0.1 mV). At each new DC boundary level, the DC characteristic is recalculated for subsequent heartbeats. The process is repeated with the DC boundary incrementally being increased until a corresponding DC characteristic is below 10%. As an alternative example, when it is determined (e.g., through a separate arrhythmia detection algorithm or during a clinical visit) that a patient is experiencing a VF episode with sensing, but the DC characteristic is below 10%, the DC boundaries may be incrementally decreased (e.g., in steps of 0.1 mV or is otherwise designated by a clinician). At each new DC boundary level, the DC characteristic is recalculated for subsequent heartbeats during the VF episode. The process repeated until the DC boundary results in a DC characteristic that is within an expected range associated with the corresponding type of VF (e.g., between 20 and 60%, between 40 and 80%, or otherwise).

Figure 6A:
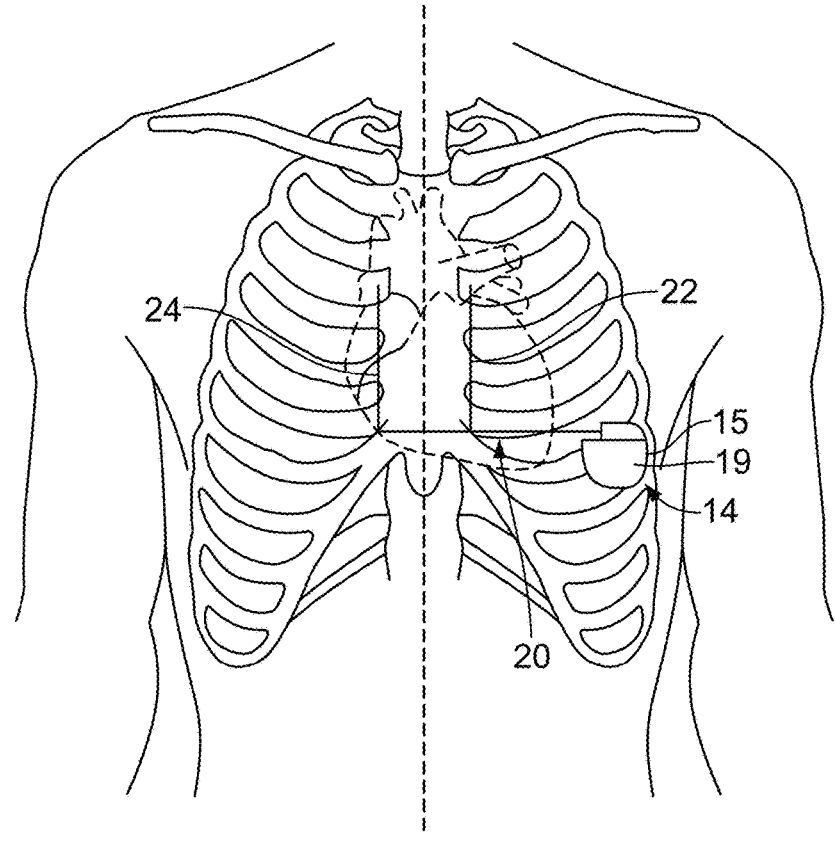
FIG. 6A illustrates a graphical representation of a subcutaneous implantable medical system that is configured to implement the methods described herein and apply therapy to a heart.
Figure 6B:
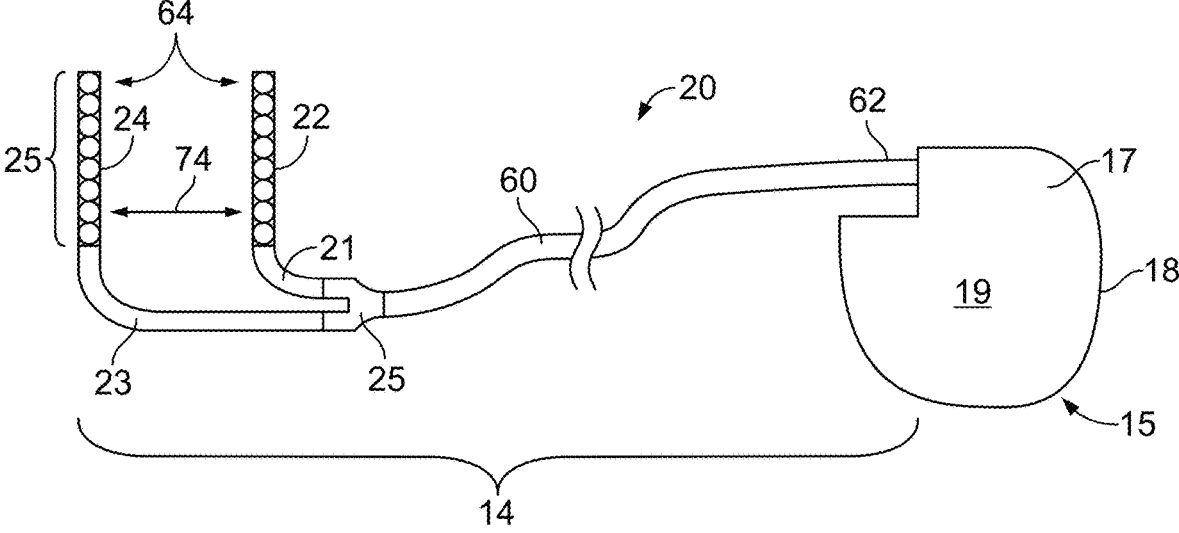
FIG. 6B illustrate a graphical representation of a subcutaneous implantable medical system that is configured to implement the methods described herein and apply therapy to a heart.

FIGS. 6A and 6B illustrate a graphical representation of a subcutaneous implantable medical system that is configured to implement the methods described herein and apply therapy to a heart. FIG. 6A illustrates a torso of a patient to show the rib cage and a general outline of the heart and greater vessels. In particular embodiments, the system may apply high voltage defibrillation shocks, as well as other general arrhythmia therapy, such as pacing therapy, cardiac resynchronization therapy (CRT), and the like. The system includes a subcutaneous implantable medical device (SIMD) 14 that is configured to be implanted in a subcutaneous area exterior to the heart. The system includes only the SIMD and is entirely or fully subcutaneous. As shown in FIG. 1A, the SIMD 14 is positioned within a lateral region, such as along the left side of the rib cage under the left arm. The SIMD 14 may be positioned relative to a vertical direction substantially aligned with the apex of the heart. The SIMD 14 is configured to deliver various arrhythmia therapies, such as defibrillation therapy, pacing therapy, anti-tachycardia pacing therapy, cardioversion therapy, and the like. It is contemplated, however, that system may include other components. For example, alternative embodiments may include a transvenous lead or a leadless electrode in addition to the structures in FIG. 6A.

The lead 20 includes one or more electrodes 22, 24 that are used for providing electrical shock for defibrillation. Optionally, the lead 20 may include one or more sensing electrodes. The pulse generator 15 may be implanted subcutaneously and at least a portion of the lead 20 may be implanted subcutaneously. In particular embodiments, the SIMD 14 is an entirely or fully subcutaneous SIMD. The pulse generator 15 may be positioned at a lateral position or below an apex of the heart.

With reference to FIG. 6B, the lead 20 includes an elongated lead body 60 that extends from a proximal end 62 to a distal tip 64. The pulse generator 15 includes a housing 18 that is configured to be active to form a pulse-generator (PG) electrode 19. The pulse generator 15 also includes a header 17 mounted to the housing 18. The header 17 is configured to receive and be connected to the proximal end 62 of the lead body 60. The proximal end 62 may include one or more contacts (not shown) that electrically engage respective terminals (not shown) in the header 17 of the pulse generator 15.

The lead body 60 may include one or more distal branches 21, 23 that separate from a splitting connector 25, where the distal branches 21, 23 each include a corresponding one of the electrodes 22, 24. The splitting connector 25 may be configured in different shapes and different manners. For example, the splitting connector 25 may be formed as a Y-connector, a T-connector and the like. The splitting connector 25 may be formed as part of a monotonic unitary body structure with the lead body 60 and distal branches 21, 23.

As shown, the lead body 60 includes two distal branches 21, 23 and two electrodes 22, 24, although it is recognized that no branch, more than two branches and more than two electrodes may be provided on the lead body 60. Additionally or alternatively, two or more separate leads 20 may be provided, with each lead 20 having a single distal segment and single electrode provided thereon. For example, the electrodes 22 and 24 may be provided on separate leads that are individually joined to the header 17. Optionally, a single lead 20 with a single electrode 22 or 24 may be used.

The electrodes 22, 24 may be referred to as first and second electrodes 22, 24 that are coupled to be electrically common with one another. The first and second electrodes 22, 24 are elongated along corresponding longitudinal axes. The first and second electrodes 22, 24 may be positioned in a dual parasternal combination extending in a common direction and spaced apart. The positioning operation may comprise positioning the first and second electrodes 22, 24 along opposite sides of the sternum, or positioning the first and second electrodes 22, 24 on a common side of the sternum. The anterior positioning operation may comprise positioning the second electrode proximate to a lower end of the sternum and orienting the second electrode to extend in a direction non-parallel to a direction of the first electrode, and locating the second electrode at a position, relative to a midline of the sternum, that is vertically below the first electrode. The non-parallel direction may orient a longitudinal axis of the second electrode perpendicular to a longitudinal axis of the first electrode.

With reference to FIG. 6A, the first electrode 22 may be positioned along a left side of the anterior region of the chest adjacent to the sternum. The second electrode 24 may be positioned along a right side of the anterior region of the chest adjacent to the sternum.

Optionally, the leads may be provided in different configurations, different locations and different combinations as explained the numerous patents and published applications references and incorporated herein.

Figure 7:
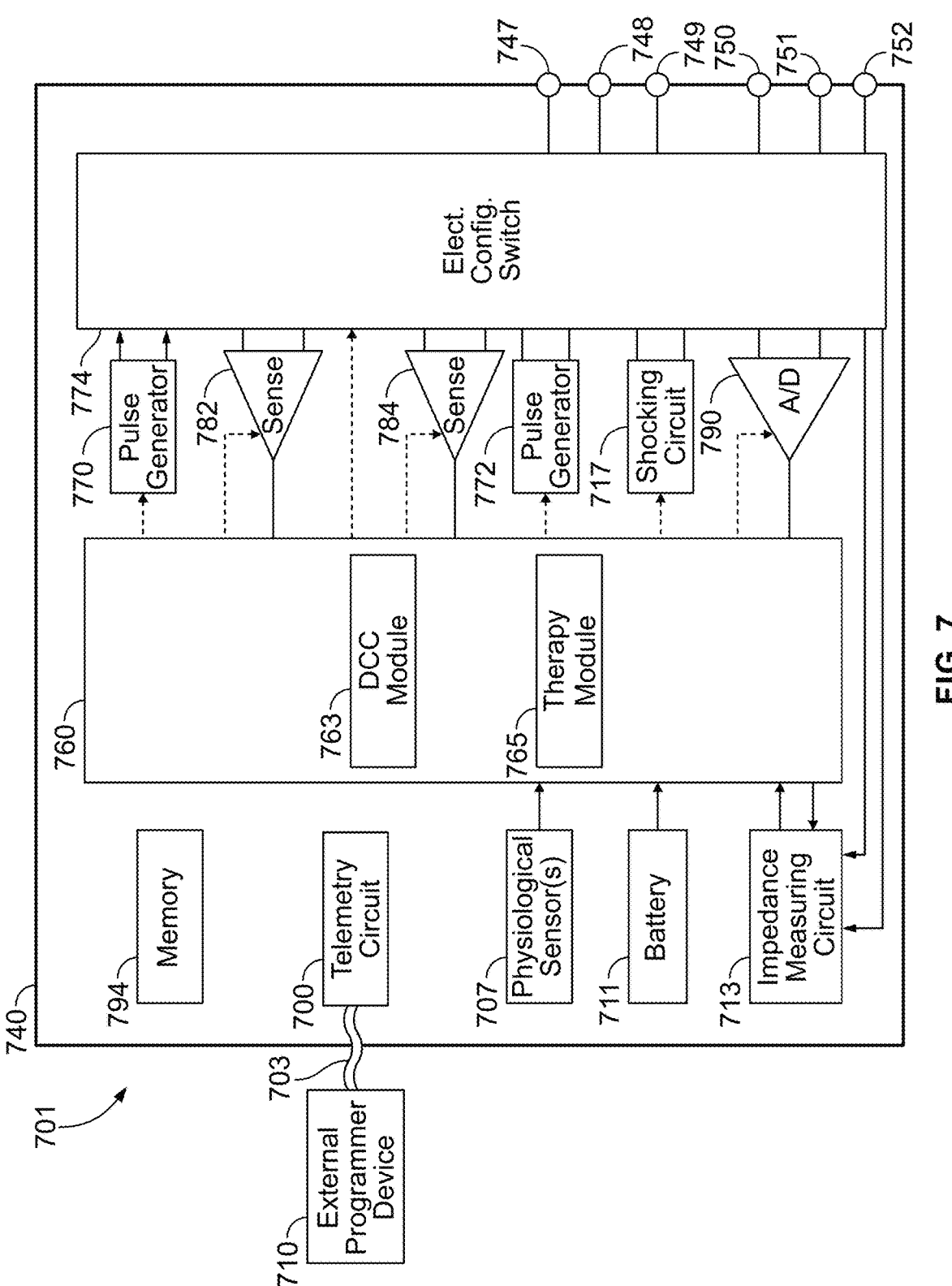
FIG. 7 illustrates a block diagram of SIMD implemented in accordance with embodiments herein.

FIG. 7 illustrates a block diagram of an SIMD 701. The SIMD 701 is capable of performing stimulation therapy, including cardioversion, defibrillation, and pacing stimulation. The SIMD 701 is hereinafter referred to as the device

710. While a particular multi-element device is shown, this is for illustration purposes only. It is understood that the appropriate circuitry could be duplicated, eliminated or disabled in any desired combination to provide a device capable of monitoring impedance and/or cardiac signals, and/or treating the appropriate chamber(s) with cardioversion, defibrillation and pacing stimulation.

The housing 740 for the device 710 is often referred to as the "canister," "can," "case," or "case electrode" and may be programmably selected to act as the shock electrode and/or as a return electrode for some or all sensing modes. The housing 740 may further be used as a return electrode alone or in combination with one or more other electrodes. The housing 740 further includes a connector (not shown) having a plurality of terminals 747-752. To achieve sensing, pacing, and shocking in connection with desired chambers of the heart, the terminals 747-752 are selectively connected to corresponding combinations of electrodes.

The device 710 includes a programmable microcontroller 760 that controls the various modes of sensing and stimulation therapy. The microcontroller 760 includes a microprocessor, or equivalent control circuitry, designed specifically for controlling sensing impedance derivation and the delivery of stimulation therapy and may further include RAM or ROM memory, logic and timing circuitry, state machine circuitry, and I/O circuitry. The microcontroller 760 includes the ability to process or monitor input signals (data) as controlled by a program code stored in memory. The details of the design and operation of the microcontroller 760 are not critical to the present invention. Rather, any suitable microcontroller 760 may be used.

The microcontroller 760 includes inputs that are configured to collect cardiac signals associated with electrical or mechanical behavior of a heart over at least one cardiac cycle. The cardiac signals may be from the cardiac sensing circuit 782 and representative of electrical behavior of the heart. The circuit 782 may provide separate, combined, composite or difference signals to the microcontroller 760 representative of the sensed signals from the electrodes. Optionally, the cardiac signals may be the output of the A/D circuit 790 that are representative of electrical behavior of the heart. The cardiac signals may be the output of the physiologic sensor 707 that are representative of mechanical behavior.

The microcontroller 760 includes a duty cycle calculation (DCC) module 763 and a therapy module 765 (among other things). The DCC module 763 is configured to calculate a DC characteristic of the modified CA signals with respect to duty cycle boundaries, and detect an arrhythmia based on the DC characteristic. The therapy module 765 is configured to deliver a corresponding therapy based on the type of arrhythmia that is detected. For example, the DCC module 763 may be configured to determine the duty cycle based on a relation between the measurement window and a segment of the modified CA signals that exceeds the duty cycle boundaries. Additionally or alternatively, the segment may be defined by an interval of time that represents a sum of a series of intervals during which the modified CA signals exceed the duty cycle boundaries, but do not exceed upper and lower sensitivity thresholds. Additionally or alternatively, the duty cycle boundaries can include a plurality of threshold levels, wherein the calculating of the DC characteristic includes determining the duty cycle characteristic based on i) determining a relation between a measurement window and a segment of the modified CA signals that exceed a first threshold level of the plurality of threshold levels, but do not exceed a second threshold level of the plurality of threshold levels, and ii) applying a weight to the modified CA signals within the segment. Additionally or alternatively, the duty cycle characteristic can further be based on i) determining a relation between the measurement window and a second segment of the modified CA signals that exceed the second threshold level but do not exceed a third threshold level of the plurality of threshold levels, and ii) applying a second weight to the modified CA signals within the second segment, wherein the first and second weights are different with respect to each other. Additionally or alternatively, the DC characteristic can be based on a plurality of segments or bands wherein the modified CA signals of a first segment exceed a first threshold level, but do not exceed a second threshold level, and the modified CA signals of a second segment exceed the second threshold level, but do not exceed a third threshold level. Additionally or alternatively, different weights (e.g., zero, a positive number, a negative number, etc.) can be applied to the percentage of time the modified CA signals are between certain threshold levels to adjust (e.g., ignore, increase, decrease, etc.) the overall impact/influence the modified CA signals have on the DC characteristic. Additionally or alternatively, the segment may be defined by area under the curve of the modified CA signals that falls between the duty cycle boundaries and the upper and lower sensitivity thresholds. The DC characteristic may correspond to an amplitude boundary limited duty cycle of the modified CA signals. The DCC module 763 is configured to determine whether the modified CA signals is indicative of an arrhythmia based on the DC characteristic. Additionally or alternatively, the microcontroller 760 can confirm at least one undersensing condition associated with at least one of a primary channel or a secondary channel in advance of determining the duty cycle characteristic, and the at least one undersensing condition can include at least one of sensing R-R intervals on an associated channel or sensing R-wave peak amplitudes on the associated channel. Additionally or alternatively, the microcontroller 760 can compare the R-R intervals to a predetermined time duration and/or determine that X out of Y of the last R-R intervals are long sensed R-R intervals.

Optionally, the microcontroller 760 may implement a primary arrhythmia detection algorithm separate and apart from the DCC module 763. The primary arrhythmia detection algorithm may be configured to analyze various characteristics of the CA signals, such as the R-R interval, variability, heart rate, etc., when declaring an arrhythmia. The DCC module 763 may further be applied as a confirmation process to utilize the DC characteristic to deny or verify arrhythmias declared by the primary arrhythmia detection algorithm.

The microcontroller 760 further controls a shocking circuit 717 by way of a control signal. The shocking circuit 717 generates stimulating pulses of low (up to 0.5 Joules), moderate (0.5-10 Joules), or high energy (11 to 50 Joules), as controlled by the microcontroller 760. Stimulating pulses may be applied to the patient's heart through at least two shocking electrodes.

One or more pulse generators 770 and 772 generate various types of therapy, such as pacing and ATP stimulation pulses for delivery by desired electrodes. The electrode configuration switch 774 (also referred to as a switch bank) controls which terminals 747-752 are connected to the pulse generators 770, 772, thereby controlling which electrodes receive a therapy. The pulse generators, 770 and 772, may include dedicated, independent pulse generators, multiplexed pulse generators, shared pulse generators or a single common pulse generator. The pulse generators 770 and 772 are controlled by the microcontroller 760 via appropriate control signals to trigger or inhibit stimulation pulses. The microcontroller 760 further includes timing control circuitry which is used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, PVARP intervals, noise detection windows, evoked response windows, alert intervals, marker channel timing, etc.

An electrode configuration switch 774 connects the sensing electronics to the desired terminals 747-752 of corresponding sensing electrodes. For example, a portion of the terminals may be coupled to electrodes configured to define a sensing and/or shocking vector that passes through the left ventricle. The switch 774 is configured to obtain far field CA signals sensed at electrodes located remote from the heart over a period of time. The sensing circuit 784 and/or software implemented by the microcontroller 760, are configured to apply a feature attenuation filter to the CA signals to form modified CA signals. The feature attenuation filter reduces potential T-waves as a feature not of interest. The circuit 784 may amplify, filter, digitize and/or otherwise process the sensed signals from the select electrodes. The sensing circuitry 74 is configured to utilize the upper and lower sensitivity thresholds in connection with sensing R waves in the CA signals.

The switch 774 also connects various combinations of the electrodes to an impedance measuring circuit 713. The impedance measuring circuit 713 includes inputs to collect multiple measured impedances between corresponding multiple combinations of electrodes. For example, the impedance measuring circuit 713 may collect a measured impedance for each or a subset of the active sensing vectors. Optionally, the impedance measuring circuit 713 may measure respiration or minute ventilation; measure thoracic impedance for determining shock thresholds; detect when the device has been implanted; measure stroke volume; and detect the opening of heart valves, etc.

The switch bank 774 includes a plurality of switches for connecting the desired electrodes to the appropriate I/O circuits, thereby providing complete electrode programmability. The switch 774, in response to a control signal from the microcontroller 760, determines the polarity of the stimulation pulses (e.g., unipolar, bipolar, co-bipolar, etc.) by selectively closing the appropriate combination of switches (not specifically shown). The outputs of the cardiac signal and event marker sensing circuits 782 and 784 are connected to the microcontroller 760 which, in turn, is able to trigger or inhibit the pulse generators 770 and 772, respectively. The sensing circuits 782 and 784, in turn, receive control signals from the microcontroller 760 for purposes of controlling the gain, threshold, the polarization charge removal circuitry (not shown), and the timing of any blocking circuitry (not shown).

Cardiac signals are also applied to the inputs of an analog-to-digital (A/D) data acquisition system 790. The data acquisition system 790 is configured to acquire cardiac signals, convert the raw analog data into a digital signal, and store the digital signals for later processing and/or telemetric transmission to an external device. The data acquisition system 790 samples cardiac signals across any pair of desired electrodes. The data acquisition system 790 may be coupled to the microcontroller 760, or other detection circuitry, for detecting an evoked response from the heart in response to an applied stimulus, thereby aiding in the detection of "capture." Capture occurs when an electrical stimulus applied to the heart is of sufficient energy to depolarize the cardiac tissue, thereby causing the heart muscle to contract.

The microcontroller 760 is further coupled to a memory 794 by a suitable data/address bus 796. The memory 794 stores programmable operating, impedance measurements, impedance derivation and therapy-related parameters used by the microcontroller 760. The operating and therapy-related parameters define, for example, pacing pulse amplitude, pulse duration, electrode polarity, rate, sensitivity, automatic features, arrhythmia detection criteria, and the amplitude, wave shape and vector of each stimulating pulse to be delivered to the patient's heart within each respective tier of therapy.

The operating and therapy-related parameters may be non-invasively programmed into the memory 794 through a telemetry circuit 700 in telemetric communication with the external device, such as a programmer, trans-telephonic transceiver, or a diagnostic system analyzer. The telemetry circuit 700 is activated by the microcontroller 760 by a control signal. The telemetry circuit 700 advantageously allows data and status information relating to the operation of the device (as contained in the microcontroller 760 or memory 794) to be sent to an external device 710 through an established communication link 703.

The device 710 may include a physiologic sensor 707 to adjust pacing stimulation rate according to the exercise state of the patient. The physiological sensor 707 may further be used to detect changes in cardiac output, changes in the physiological condition of the heart, or diurnal changes in activity (e.g., detecting sleep and wake states). The battery 711 provides operating power to all of the circuits.

IMDs and Processes to Implement in Accordance with Embodiments

Embodiments may be implemented in connection with one or more implantable medical devices (IMDs). Non-limiting examples of IMDs include one or more of implantable leadless monitoring and/or therapy devices, transvenous devices, subcutaneous devices, and/or alternative implantable medical devices. For example, the IMD may represent a cardiac monitoring device, pacemaker, cardioverter, cardiac rhythm management device, defibrillator, leadless monitoring device, leadless pacemaker and the like. For example, the IMD may include one or more structural and/or functional aspects of the device(s) described in U.S. Pat. No. 9,216,285, entitled "LEADLESS IMPLANTABLE MEDICAL DEVICE HAVING REMOVABLE AND FIXED COMPONENTS" issued Dec. 22, 2015; U.S. Pat. No. 8,391,980, entitled "METHOD AND SYSTEM FOR IDENTIFYING A POTENTIAL LEAD FAILURE IN AN IMPLANTABLE MEDICAL DEVICE" issued Mar. 5, 2013 and U.S. Pat. No. 9,232,485, entitled "SYSTEM AND METHOD FOR SELECTIVELY COMMUNICATING WITH AN IMPLANTABLE MEDICAL DEVICE" issued Jan. 5, 2016; U.S. application Ser. No. 15/973,195, entitled "SUBCUTANEOUS IMPLANTATION MEDICAL DEVICE WITH MULTIPLE PARASTERNAL-ANTERIOR ELECTRODES" filed May 7, 2018; U.S. application Ser. No. 15/973,219, entitled "IMPLANTABLE MEDICAL SYSTEMS AND METHODS INCLUDING PULSE GENERATORS AND LEADS" filed May 7, 2018; U.S. application Ser. No. 15/973,249, entitled "SINGLE SITE IMPLANTATION METHODS FOR MEDICAL DEVICES HAVING MULTIPLE LEADS", filed May 7, 2018; U.S. application Ser. No. 15/973,219, entitled "IMPLANTABLE MEDICAL SYSTEMS AND METHODS INCLUDING PULSE GENERATORS AND LEADS", filed May 7, 2018;

U.S. application Ser. No. 15/973,195, entitled "SUBCUTANEOUS IMPLANTATION MEDICAL DEVICE WITH MULTIPLE PARASTERNAL-ANTERIOR ELECTRODES"; U.S. patent application Ser. No. 15/973,126, titled "METHOD AND SYSTEM FOR SECOND PASS CONFIRMATION OF DETECTED CARDIAC ARRHYTHMIC PATTERNS"; U.S. patent application Ser. No. 15/973,351, titled "METHOD AND SYSTEM TO DETECT R-WAVES IN CARDIAC ARRHYTHMIC PATTERNS"; U.S. patent application Ser. No. 15/973,307, titled "METHOD AND SYSTEM TO DETECT POST VENTRICULAR CONTRACTIONS IN CARDIAC ARRHYTHMIC PATTERNS"; and U.S. patent application Ser. No. 16/399,813, titled "METHOD AND SYSTEM TO DETECT NOISE IN CARDIAC ARRHYTHMIC PATTERNS"; U.S. patent application Ser. No. 16/930,791, filed Jul. 16, 2020, and titled "METHODS, DEVICES AND SYSTEMS FOR HOLISTIC INTEGRATED HEALTHCARE PATIENT MANAGEMENT"; U.S. Patent Publication Number 2014/0275827, entitled "METHOD AND SYSTEM FOR DERIVING EFFECTIVENESS OF MEDICAL TREATMENT OF A PATIENT" published Sep. 18, 2014; U.S. Patent Publication Number 2013/0204147, entitled "ATRIAL FIBRILLATION DETECTION BASED ON PULMONARY ARTERY PRESSURE DATA" published Aug. 8, 2013; U.S. Patent Publication Number 2012/0089032, entitled "METHOD AND SYSTEM FOR DISCRIMINATING AND MONITORING ATRIAL ARRHYTHMIA BASED ON CARDIOGENIC IMPEDANCE" published Apr. 12, 2012; U.S. Patent Publication Number 2011/0125206, entitled "SINGLE CHAMBER IMPLANTABLE MEDICAL DEVICE FOR CONFIRMING ARRHYTHMIA THROUGH RETROSPECTIVE CARDIAC SIGNALS" published May 26, 2011; U.S. Patent Publication Number 2014/0058278, entitled "SYSTEMS AND METHODS FOR DETECTING ISCHEMIC EVENTS" published Feb. 27, 2014; U.S. Patent Publication Number 2013/0218036, entitled "METHODS AND SYSTEMS TO CORRELATE ARRHYTHMIC AND ISCHEMIC EVENTS" published Aug. 22, 2013; U.S. Patent Publication Number 2012/0197149, entitled "SYSTEM AND METHOD FOR DISTINGUISHING AMONG CARDIAC ISCHEMIA, HYPOGLYCEMIA AND HYPERGLYCEMIA USING AN IMPLANTABLE MEDICAL DEVICE" published Aug. 2, 2012; U.S. Patent Publication Number 2012/0065527, entitled "METHODS AND SYSTEMS FOR MONITORING ATRIAL STIFFNESS" published Mar. 15, 2012; U.S. Patent Publication Number 2012/0046528, entitled "SYSTEM AND METHOD FOR DETECTING AND TREATING CARDIOVASCULAR DISEASE" published Feb. 23, 2012; U.S. Patent Publication Number 2011/0004111, entitled "ISCHEMIA DETECTION USING INTRA-CARDIAC SIGNALS" published Jan. 6, 2011; and/or U.S. Pat. No. 8,514,086, entitled "DISPLAYS FOR A MEDICAL DEVICE", issued Aug. 20, 2013, all of which are incorporated by reference entirely.

All references, including publications, patent applications and patents, cited herein are hereby incorporated by reference to the same extent as if each reference were individually and specifically indicated to be incorporated by reference and were set forth in its entirety herein.

Closing Statements

It should be clearly understood that the various arrangements and processes broadly described and illustrated with respect to the Figures, and/or one or more individual components or elements of such arrangements and/or one or more process operations associated of such processes, can be employed independently from or together with one or more other components, elements and/or process operations described and illustrated herein. Accordingly, while various arrangements and processes are broadly contemplated, described and illustrated herein, it should be understood that they are provided merely in illustrative and non-restrictive fashion, and furthermore can be regarded as but mere examples of possible working environments in which one or more arrangements or processes may function or operate.

As will be appreciated by one skilled in the art, various aspects may be embodied as a system, method or computer (device) program product. Accordingly, aspects may take the form of an entirely hardware embodiment or an embodiment including hardware and software that may all generally be referred to herein as a "circuit," "module" or "system." Furthermore, aspects may take the form of a computer (device) program product embodied in one or more computer (device) readable storage medium(s) having computer (device) readable program code embodied thereon.

Any combination of one or more non-signal computer (device) readable medium(s) may be utilized. The non-signal medium may be a storage medium. A storage medium may be, for example, an electronic, magnetic, optical, electromagnetic, infrared, or semiconductor system, apparatus, or device, or any suitable combination of the foregoing. More specific examples of a storage medium would include the following: a portable computer diskette, a hard disk, a random access memory (RAM), a dynamic random access memory (DRAM), a read-only memory (ROM), an erasable programmable read-only memory (EPROM or Flash memory), a portable compact disc read-only memory (CD-ROM), an optical storage device, a magnetic storage device, or any suitable combination of the foregoing.

Program code for carrying out operations may be written in any combination of one or more programming languages. The program code may execute entirely on a single device, partly on a single device, as a stand-alone software package, partly on single device and partly on another device, or entirely on the other device. In some cases, the devices may be connected through any type of network, including a local area network (LAN) or a wide area network (WAN), or the connection may be made through other devices (for example, through the Internet using an Internet Service Provider) or through a hard wire connection, such as over a USB connection. For example, a server having a first processor, a network interface, and a storage device for storing code may store the program code for carrying out the operations and provide this code through its network interface via a network to a second device having a second processor for execution of the code on the second device.

Aspects are described herein with reference to the Figures, which illustrate example methods, devices and program products according to various example embodiments. These program instructions may be provided to a processor of a general purpose computer, special purpose computer, or other programmable data processing device or information handling device to produce a machine, such that the instructions, which execute via a processor of the device implement the functions/acts specified. The program instructions may also be stored in a device readable medium that can direct a device to function in a particular manner, such that the instructions stored in the device readable medium produce an article of manufacture including instructions which implement the function/act specified. The program instructions may also be loaded onto a device to cause a series of operational steps to be performed on the device to produce a device implemented process such that the instructions which execute on the device provide processes for implementing the functions/acts specified.

The units/modules/applications herein may include any processor-based or microprocessor-based system including systems using microcontrollers, reduced instruction set computers (RISC), application specific integrated circuits (ASICs), field-programmable gate arrays (FPGAs), logic circuits, and any other circuit or processor capable of executing the functions described herein. Additionally or alternatively, the modules/controllers herein may represent circuit modules that may be implemented as hardware with associated instructions (for example, software stored on a tangible and non-transitory computer readable storage medium, such as a computer hard drive, ROM, RAM, or the like) that perform the operations described herein. The above examples are exemplary only, and are thus not intended to limit in any way the definition and/or meaning of the term "controller." The units/modules/applications herein may execute a set of instructions that are stored in one or more storage elements, in order to process data. The storage elements may also store data or other information as desired or needed. The storage element may be in the form of an information source or a physical memory element within the modules/controllers herein. The set of instructions may include various commands that instruct the modules/applications herein to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings herein without departing from its scope. While the dimensions, types of materials and coatings described herein are intended to define various parameters, they are by no means limiting and are illustrative in nature. Many other embodiments will be apparent to those of skill in the art upon reviewing the above description. The scope of the embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects or order of execution on their acts.

Further, the limitations of the following claims are not written in means-plus-function format and are not intended to be interpreted based on 35 U.S.C. § 112(f) unless and until such claim limitations expressly use the phrase "means for" followed by a statement of function void of further structure.

What is claimed is:

1. A computer implemented method for detecting an arrhythmia, comprising, under control of one or more processors configured with executable instructions:

sensing far field cardiac activity (CA) signals at electrodes located remote from a heart over a period of time;

applying a feature attenuation filter to the CA signals to form modified CA signals, the feature attenuation filter reducing potential T-waves as a feature not of interest;

calculating a duty cycle (DC) characteristic of the modified CA signals with respect to upper and lower duty cycle boundaries and upper and lower sensitivity thresholds, wherein the upper duty cycle boundary having a positive voltage level and the lower duty cycle boundary having a negative voltage level, wherein the upper and lower duty cycle boundaries are at levels within the upper and lower sensitivity thresholds;

detecting an arrhythmia based on the DC characteristic; and delivering a therapy based on detection of the arrhythmia.

2. The method of claim 1, further comprising defining a duration of a measurement window, wherein the calculating includes determining the duty cycle characteristic based on a relation between the measurement window and a segment of the modified CA signals that exceed the upper or lower duty cycle boundaries but do not exceed the upper or lower sensitivity thresholds.

3. The method of claim 2, further comprising: determining a series of intervals during which the modified CA signals exceed the upper or lower duty cycle boundaries, but do not exceed the upper or lower sensitivity thresholds; summing the series of intervals; and defining the segment by an interval of time that represents a sum of the series of intervals.

4. The method of claim 3, further comprising identifying R-waves in the CA signals that exceed the upper and lower sensitivity thresholds.

5. The method of claim 2, further comprising determining regions representing area under the curve of the modified CA signals that falls between the upper duty cycle boundary and the upper sensitivity threshold or the lower duty cycle boundary and the lower sensitivity threshold; and defining the segment based on an area of the regions.

6. The method of claim 1, wherein the upper and lower duty cycle boundaries correspond to amplitude boundaries of the modified CA signals.

7. The method of claim 1, further comprising implementing the sensing and applying operations by an implantable medical device; and determining the calculating and detecting operations by an external device.

8. The method of claim 1, further comprising applying a primary arrhythmia detection algorithm to declare arrhythmias, the one or more processors further configured to utilize the DC characteristic as a confirmation process to deny or verify the arrhythmias declared by the primary arrhythmia detection algorithm.

9. The method of claim 1, further comprising: determining one or more characteristics of interest from the CA signals; and dynamically adjusting the upper and lower duty cycle boundaries based on the one or more characteristics of interest from the CA signals.

10. The method of claim 1, further comprising defining a duration of a measurement window, wherein the upper and lower duty cycle boundaries further comprise a plurality of threshold levels, wherein the calculating further includes determining the duty cycle characteristic based on i) determining a relation between the measurement window and a segment of the modified CA signals that exceed a first threshold level of the plurality of threshold levels, but do not exceed a second threshold level of the plurality of threshold levels, and ii) applying a weight to the modified CA signals within the segment.

11. The method of claim 10, wherein the calculating further includes determining the duty cycle characteristic is further based on i) determining a relation between the measurement window and a second segment of the modified CA signals that exceed the second threshold level but do not exceed a third threshold level of the plurality of threshold levels, and ii) applying a second weight to the modified CA signals within the second segment, wherein the first and second weights are different with respect to each other.

12. A system for detecting arrhythmias, comprising:

electrodes configured to sense far field cardiac activity (CA) signals over a period of time, the electrodes configured to be located remote from a heart;

a feature attenuation filtering circuit configured to apply a feature attenuation filter to the CA signals to form modified CA signals, the feature attenuation filter reducing potential T-waves as a feature not of interest;

memory to store specific executable instructions; and one or more processors, that when executing the specific executable instructions, are configured to:

define upper and lower duty cycle boundaries and upper and lower sensitivity thresholds, wherein the upper duty cycle boundary having a positive voltage level and the lower duty cycle boundary having a negative voltage level, wherein the upper and lower duty cycle boundaries are at levels within the upper and lower sensitivity thresholds;

calculate a duty cycle (DC) characteristic of the modified CA signals with respect to the upper and lower duty cycle boundaries and the upper and lower sensitivity thresholds;

detect an arrhythmia based on the DC characteristic; and deliver a therapy based on detection of the arrhythmia.

13. The system of claim 12, wherein the one or more processors are further configured to: define a duration of a measurement window; and determine the duty cycle characteristic based on a relation between the measurement window and a segment of the modified CA signals that exceed the upper or lower duty cycle boundaries but do not exceed the upper and lower sensitivity thresholds.

14. The system of claim 13, wherein the one or more processors are further configured to determine a series of intervals during which the modified CA signals exceed the upper or lower duty cycle boundaries, but do not exceed the upper or lower sensitivity thresholds; sum the series of intervals; and define the segment by an interval of time that represents the sum of the series of intervals.

15. The system of claim 14, further comprising sensing circuitry configured to utilize the upper and lower sensitivity thresholds in connection with sensing R waves in the CA signals.

16. The system of claim 13, wherein the one or more processors are further configured to determine regions representing area under the curve of the modified CA signals that falls between the upper duty cycle boundary and the upper sensitivity threshold or the lower duty cycle boundary and the lower sensitivity threshold; and define the segment based on an area of the regions.

17. The system of claim 12, wherein the upper and lower duty cycle boundaries correspond to amplitude boundaries of the modified CA signals.

18. The system of claim 12, further comprising: an implantable medical device configured to include the electrodes and feature attenuation filtering circuit; and an external device configured to include the one or more processors that are configured to implement the calculate and detect operations.

19. The system of claim 12, wherein the one or more processors are further configured to: determine one or more characteristics of interest from the CA signals; and dynamically adjust the upper and lower duty cycle boundaries based on the one or more characteristics of interest from the CA signals.

20. The system of claim 12, wherein the feature attenuation filtering circuit represent a bandpass filter having a passband at 8-15 Hz.

21. The system of claim 12, further comprising at least one of a primary channel or a secondary channel associated with the electrodes, wherein the one or more processors are further configured to confirm at least one undersensing condition in advance of calculating the duty cycle characteristic, the at least one undersensing condition based on the CA signals sensed by the at least one of a primary channel or a secondary channel and filtered by the feature attenuation filtering circuit, wherein the at least one undersensing condition includes at least one of sensing R-R intervals or sensing R-wave peak amplitudes.

22. The system of claim 21, wherein the one or more processors are further configured to compare the R-R intervals to a predetermined time duration or to determine that X out of Y of the last R-R intervals are long sensed R-R intervals.

\* \* \* \* \*